United States Patent [19]
Hallahan

[11] Patent Number: 6,159,443
[45] Date of Patent: Dec. 12, 2000

[54] X-RAY GUIDED DRUG DELIVERY

[75] Inventor: Dennis E. Hallahan, Nashville, Tenn.

[73] Assignee: Vanderbilt University, Nashville, Tenn.

[21] Appl. No.: 09/302,456

[22] Filed: Apr. 29, 1999

[51] Int. Cl.$^7$ .......................... A61K 51/00; A01N 63/00; C12Q 1/68; C12N 15/63; C07H 21/04
[52] U.S. Cl. ................ 424/1.17; 424/9.1; 424/93.72; 435/6; 435/320.1; 435/455; 536/23.1
[58] Field of Search ..................... 424/1.17, 9.1, 424/93.72; 435/6, 455, 320.1; 536/23.1

[56] References Cited

U.S. PATENT DOCUMENTS

| | | | |
|---|---|---|---|
| 4,515,165 | 5/1985 | Carroll | 600/475 |
| 4,670,386 | 6/1987 | Sugaar | 435/29 |
| 5,292,524 | 3/1994 | Male et al. | 424/1.17 |
| 5,328,840 | 7/1994 | Coller | 435/7.25 |
| 5,334,369 | 8/1994 | Halushka et al. | 424/1.85 |
| 5,382,680 | 1/1995 | Abraham et al. | 562/451 |
| 5,516,881 | 5/1996 | Lee et al. | 528/320 |
| 5,693,627 | 12/1997 | Schieven | 514/137 |
| 5,759,542 | 6/1998 | Gurewich | 424/94.64 |

FOREIGN PATENT DOCUMENTS

WO 93/14791 A2  8/1993  WIPO.

OTHER PUBLICATIONS

Weilchselbaum et al. Gene therapy targeted by radiation preferentially radiosensitizes tumor cells. Cancer Res. vol. 54:4266–4269, Aug. 1994.

Hirata et al. Artificial matastases and decrease of frbrinolysis in the nude mouse lung after hemithoracic irradiation. Clin Expl. Metastasis. Vol. 2:3311–319, Oct. 1984.

Hirata et al. Fate of intravenously injected human tumor cells in the lung of nude mice following whole body X–irradiation. Invasion Metastasis. Vol. 5:61–70, Jul. 1985.

Stratton et al. Imaging arterial thrombosis: Comparison of technetium–99m–labelled monoclonal antifibrin antibodies and indium–111–platelets. J. nucl. Med. vol. 35:1731–1737, Nov. 1994.

*Primary Examiner*—Robert A. Schwartzman
*Assistant Examiner*—William Sandals
*Attorney, Agent, or Firm*—Jenkins & Wilson, P.A.

[57] ABSTRACT

A method of delivering an active agent to a target tissue, particularly neoplastic tissue, vascular anomaly or tumor tissue, in a vertebrate subject. The method includes the steps of exposing the target tissue to ionizing radiation; and administering a delivery vehicle to the vertebrate subject before, after, during, or combinations thereof, exposing the target tissue to the ionizing radiation. The delivery vehicle includes the active agent and delivers the agent to the target tissue. Exemplary delivery vehicles include platelets; leukocytes; proteins or peptides which bind activated platelets; antibodies which bind activated platelets; microspheres coated with proteins or peptides which bind activated platelets; liposomes conjugated to platelets, leukocytes, proteins or peptides which bind activated platelets, or antibodies which bind activated platelets; and combinations thereof.

104 Claims, No Drawings

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:  peptide
      linker

<400> SEQUENCE: 1

Leu Ala Leu Ala
```

X-RAY GUIDED DRUG DELIVERY

GRANT STATEMENT

This invention was made in part from government support under Grant Nos. CA70937 and CA58508 from the National Institute of Health. Thus, the U.S. Government has certain rights in the invention.

TECHNICAL FIELD

The present invention relates to a method for selective in vivo delivery of therapeutic or imaging agents. More particularly, the present invention relates to method for selective in vivo delivery of therapeutic or imaging agents using ionizing radiation as a guide for the selective delivery.

TABLE OF ABBREVIATIONS

AcNPV—*Autograph californica* nuclear polyhidrosis virus
AVM—arteriovenous malformation(s)
BPR—bovine pancreatic ribonuclease
CAM—cell adhesion molecule
CaMV—Cauliflower mosaic virus
cGy—centiGray
Gy—Gray
CD62P—P-selectin
CD63—cell adhesion molecule 63
CT—computed tomography
DDAVP—depoprovera
DT—diphtheria toxin
ELISA—enzyme linked immunosorbent assay
GEL—gelonin
GP-IIb—platelet membrane glycoprotein IIb
GP-IIIa—platelet membrane glycoprotein IIIa
GST—glutathione S-transferase
h or hr—hour(s)
HUVEC—human umbilical vein endothelial cells
IL-8—interleukin-8
keV—kiloelectron volts
kV—kilovolt(s)
min—minute(s)
MRI—nuclear magnetic resonance imaging
MV—megavolt(s)
nM—nanomoles
PBS—phosphate buffered saline
PPP—platelet poor plasma
PRP—platelet rich plasma
PAP—pokeweed antiviral protein
PE—Pseudomonas exotoxin
PET—positron emission tomography
RES—reticular endothelial system
RSVE—reconstituted Sendai virus envelopes
SAP—saporin
SMPT—4-succinimidyloxycarbonyl-methyl-(2-pyridyldithio)-toluene
SPDP—N-succinimidyl-3-(2-pyridyldithio)propionate
SPECT—single photon emission computed tomography
TMV—Tobacco mosaic virus
WPB—Weibel-Palade body

BACKGROUND ART

Ionizing radiation has been used to attenuate bleeding from tumors for the past three decades. See G. H. Fletcher, *Textbook of Radiotherapy*. Philadelphia, Lea and Febiger (1975). The primary examples of this use are in the treatment of menorrhagia from cervical carcinoma, hemoptysis from lung cancer and gastrointestinal bleeding from rectal and gastric carcinomas. The dose that is recommended to control bleeding from tumors is 400 to 500 cGy/fraction given for three consecutive days, as described by G. H. Fletcher, *Textbook of Radiotherapy*, Philadelphia, Lea and Febiger (1975) and by A. M. Markoe, *Radiation Oncologic Emergencies*, in *Principles and Practice of Radiation Oncology* 1267–1270 (1987). However, the efficacy of this regimen is not well documented. Moreover, the mechanism of radiation-induced control of bleeding is unknown.

Currently practiced methods of tumor specific drug delivery involve the use of antibody conjugates to liposomes and viral vectors. These methods are specific for tumor subtype or are nonspecific in localization. These limitations are significant in that, on the one hand, only certain types of tumors may be treated and, on the other hand, nonspecific localization produces undesirable collateral damage to otherwise healthy tissue.

Techniques for loading platelets have been disclosed in the art. For example, U.S. Pat. No. 5,292,524 issued to Male et al. on Mar. 8, 1994 discloses the preparation of loaded blood platelets which include a loading vehicle selected from the group consisting of liposomes and reconstituted Sendai virus envelopes. A diagnostic or therapeutic agent is encapsulated within the loading vehicle. However, there is no disclosure of a targeting technique for the loaded platelets.

U.S. Pat. No. 5,328,840 issued Jul. 12, 1994 to Coller discloses a method for preparing a targeted carrier erythrocyte by conjugating the erythrocyte with a particular polypeptide sequence. Thus, the targeting technique disclosed in Coller involves a complicated conjugation reaction.

In view of the shortcomings of the aforementioned techniques, there remains significant need in the field for advances in the tissue-selective delivery of therapeutic and imaging agents. Moreover, there remains a substantial need in the art for an improved method for the selective delivery of therapeutic or imaging agents to neoplastic tissue. Indeed, a particularly desirable method would provide for the specific delivery of a therapeutic or imaging agent to a wide variety of neoplasms while at the same time would maintain specificity for neoplastic tissue. Such a method is currently not available in the art.

DISCLOSURE OF THE INVENTION

A method of targeting a tissue in a vertebrate subject for delivery of an active agent is disclosed. The method comprises the step of exposing the tissue to ionizing radiation before, after, during, or combinations thereof, administration of a delivery vehicle comprising the active agent to the vertebrate subject.

A method of delivering an active agent to a target tissue in a vertebrate subject is also disclosed. The method comprises the steps of exposing the target tissue to ionizing radiation; and administering a delivery vehicle to the vertebrate subject before, after, during, or combinations thereof, exposing the target tissue to the ionizing radiation, the delivery vehicle comprising the active agent, whereby the delivery vehicle aggregates in the target tissue to thereby deliver the agent to the target tissue.

Neoplasms and vascular anomalies comprise examples of target tissues. Therapeutic and imaging agents are particularly contemplated active agents. Thus, a method of treating a neoplasm in a vertebrate subject is also disclosed herein.

It is therefore an object of the present invention to provide an improved method for selectively delivering an active agent to a target tissue, and particularly to neoplastic tissue or vascular anomaly, in a vertebrate subject.

It is another object of the present invention to provide a method for delivering an active agent to a neoplasm in a vertebrate subject which is applicable to a wide variety of neoplasms.

It is a further object of the present invention to provide a method for selectively delivering an active agent to a neoplasm in a vertebrate subject which provides for the selective delivery of the active agent using a noninvasive targeting step.

Some of the objects of the invention having been stated hereinabove, other objects will become evident as the description proceeds, when taken in connection with the accompanying Examples as best described hereinbelow.

DETAILED DESCRIPTION OF THE INVENTION

Disclosed herein is the surprising observation that platelets aggregate in tumor vessels in a dose and time dependent manner when the tumor is irradiated with ionizing radiation, such as X-radiation. A method for delivering an active agent to a target tissue, such as tumor tissue or other neoplastic tissue, using a delivery vehicle comprising the active agent, and using ionizing radiation to target the tissue of interest is thus contemplated in accordance with the present invention.

Also disclosed herein is the surprising observation that expression of the cell adhesion molecule P-selectin is localized in the vascular lumen of tumor blood vessels when the tumor is irradiated. This observation was made in a wide variety of tumors. Although applicant does not wish to be bound by any particular theory of operation, it is contemplated that P-selectin mediates platelet aggregation in irradiated tumor blood vessels.

While the following terms are believed to be well understood by one of ordinary skill in the art, the following definitions are set forth to facilitate explanation of the invention.

The term "ionizing radiation" is meant to refer to any radiation where a nuclear particle has sufficient energy to remove an electron or other particle from an atom or molecule, thus producing an ion and a free electron or other particle. Examples of such ionizing radiation include, but are not limited to, gamma rays, X-rays, protons, electrons and alpha particles. Ionizing radiation is commonly used in medical radiotherapy and the specific techniques for such treatment will be apparent to a skilled practitioner in the art.

The term "delivery vehicle" as used herein is meant to refer to any cell, molecule, peptide, conjugate, article or other vehicle as would be appreciated by one of ordinary skill in the art after reviewing the disclosure of the present application that can be used to carry an active agent to a target tissue in accordance with the present invention. A particularly contemplated delivery vehicle is characterized by an ability to preferentially bind activated platelets. More particularly, contemplated delivery vehicles include, but are not limited to, platelets; leukocytes; proteins or peptides which bind activated platelets; antibodies which bind activated platelets; microspheres coated with proteins or peptides which bind activated platelets; liposomes conjugated to platelets, leukocytes, proteins or peptides which bind activated platelets, or antibodies which bind activated platelets; and combinations thereof.

The term "active agent" is meant to refer to compounds that are therapeutic agents or imaging agents.

The term "therapeutic agent" is meant to refer to any agent having a therapeutic effect, including but not limited to chemotherapeutics, toxins, radiotherapeutics, or radiosensitizing agents.

The term "chemotherapeutic" is meant to refer to compounds that, when contacted with and/or incorporated into a cell, produce an effect on the cell, including causing the death of the cell, inhibiting cell division or inducing differentiation.

The term "toxin" is meant to refer to compounds that, when contacted with and/or incorporated into a cell, produce the death of the cell.

The term "radiotherapeutic" is meant to refer to radionuclides which when contacted with and/or incorporated into a cell, produce the death of the cell.

The term "radiosensitizing agent" is meant to refer to agents which increase the susceptibility of cells to the damaging effects of ionizing radiation or which become more toxic to a cell after exposure of the cell to ionizing radiation. A radiosensitizing agent permits lower doses of radiation to be administered and still provide a therapeutically effective dose.

The term "imaging agent" is meant to refer to compounds which can be detected.

The term "neoplasm" is meant to refer to an abnormal mass of tissue or cells. The growth of these tissues or cells exceeds and is uncoordinated with that of the normal tissues or cells and persists in the same excessive manner after cessation of the stimuli which evoked the change. These neoplastic tissues or cells show a lack of structural organization and coordination relative to normal tissues or cells which usually results in a mass of tissues or cells which can be either benign or malignant. Contemplated neoplasms thus include all forms of cancer, benign intracranial neoplasms, and aberrant blood vessels such as arteriovenous malformations (AVM), angiomas, macular degeneration, and other such vascular anomalies. As would be apparent to one of ordinary skill in the art, the term "tumor" typically refers to a larger neoplastic mass.

As used herein, neoplasm includes any neoplasm, including particularly all forms of cancer. This includes, but is not limited to, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, and the like. This also includes, but is not limited to, solid tumors, solid tumor metastases, angiofibromas, retrolental fibroplasia, hemangiomas, Karposi's sarcoma and the like cancers which require neovascularization to support tumor growth.

The phrase "treating a neoplasm" includes, but is not limited to, halting the growth of the neoplasm, killing the neoplasm, reducing the size of the neoplasm, or obliterating a neoplasm comprising a vascular anomaly. Halting the growth of the neoplasm refers to halting any increase in the size of the neoplasm or the neoplastic cells, or halting the division of the neoplasm or the neoplastic cells. Reducing the size of the neoplasm relates to reducing the size of the neoplasm or the neoplastic cells.

The term "subject" as used herein refers to any target of the treatment. Also provided by the present invention is a method of treating neoplastic cells which were grown in tissue culture. Also provided by the present invention is a method of treating neoplastic cells in situ, or in their normal position or location, for example, neoplastic cells of breast or prostate tumors. These in situ neoplasms can be located within or on a wide variety of hosts; for example, human hosts, canine hosts, feline hosts, equine hosts, bovine hosts, porcine hosts, and the like. Any host in which is found a neoplasm or neoplastic cells can be treated and is accordance with the present invention.

The terms "pharmaceutically acceptable", "physiologically tolerable" and grammatical variations thereof, as they refer to compositions, carriers, diluents and reagents, are used interchangeably and represent that the materials are capable of administration to or upon a vertebrate subject without the production of undesirable physiological effects such as nausea, dizziness, gastric upset and the like.

A. General Considerations

Weibel-Palade bodies contain several proteins and proteoglycans that initiate thrombosis and inflammation. These include P-selectin, von Willebrand factor, IL-8 and CD63. To determine whether x-rays produce exocytosis of Weibel-Palade bodies (WPB), the vasculature within the mouse thorax was irradiated and immunohistochemistry for P-selectin was performed. Rapid exocytosis of WPB was observed within 30 minutes of X-irradiation. HUVEC endothelial cells were utilized to study the mechanisms of radiation-mediated WPB exocytosis in vitro. Exocytosis was most efficient at 2 to 5 Gy, whereas higher doses cause apoptosis in endothelial cells which interferes with exocytosis.

P-selectin is a cell adhesion molecule that is sequestered in storage reservoirs within the vascular endothelium and alpha granules in platelets. P-selectin is rapidly translocated to the vascular lumen after tissue injury to initiate the adhesion and activation of platelets and leukocytes. The histologic pattern of P-selectin expression in irradiated tumor blood vessels was studied.

GP-IIb and GP-IIIa are platelet antigens that are not found in the vascular endothelium. Anti-GP-IIb and anti-GP-IIIa antibodies were utilized to determine whether the time-dependent increase in P-selectin staining is due to platelet aggregation. Lewis lung carcinoma tumors in C57BL6 mice were irradiated and stained with anti-GP-IIb and anti-GP-IIIa antibodies. Little GP-IIb or GP-IIIa staining was observed in blood vessels at 1 hour following irradiation. However, GP-IIb and GP-IIIa staining increased at 6 and 24 hours following irradiation. These findings indicate that the increased P-selectin staining within the vascular lumen of irradiated tumors was, in part, due to platelet aggregation.

To verify that platelet aggregation was present in these irradiated blood vessels, tissue sections were stained with anti-GP-IIb and anti-GPIIIa antibodies that stained the platelets. No P-selectin, GP-IIb, or GP-IIIa staining was observed in the brain or kidney, but P-selectin, GP-IIb, and GP-IIIa staining were present in the irradiated lung, intestine and tumor vessels. The P-selectin knockout mouse was used to study the correlation between platelet aggregation (i.e. GPIIb or GP-IIIa accumulation) and P-selectin staining in the vascular endothelium. The GP-IIb and GP-IIIa staining was not localized to the lumen of irradiated blood vessels in the knockout mouse, but extravasated into the irradiated lung, intestine and tumors. Red blood cells also extravasated from irradiated tissues. Therefore, P-selectin accumulation in irradiated blood vessels correlated with maintenance of the barrier function of the endothelium, and knockout of the P-selectin gene leads to extravasation of platelets and red blood cells.

Animal studies using rats demonstrated that P-selectin is localized within the endothelium of tumor blood vessels prior to irradiation. One to six hours following irradiation, P-selectin is mobilized to the lumen of the blood vessel. This is not a tumor or species-specific event. There was no increase in P-selectin staining at 1 Gy but efficient localization occurred with 2, 4, 10 and 20 Gy. P-selectin staining of tumors increased over 24 hours following 10 Gy but not 2 Gy.

The radiation-induced increase in P-selectin was shown to result in platelet aggregation. Immunohistochemical studies using GP-IIb and GP-IIIa revealed the P-selectin is of platelet, not endothelial, origin. Using anti-GP-IIb and anti-GP-IIIa antibodies there was increased staining 6 and 24 hours after radiation. Animal studies using immunofluorescent staining of platelet aggregates demonstrated that radiation-induced platelet aggregation occurs in tissues that express P-selectin such as lung, colon, small intestine and tumors, whereas, it is absent in tissues such as brain, lung and kidney where there is an absence of P-selectin.

Animal studies have also shown that radiation-induced platelet aggregation occurs in tumor cells but not in surrounding P-selectin deficient normal tissue. Therefore, the method of the present invention contemplates the selective targeting of tumors by delivering radiation to target tumors to induce platelet aggregation in tumors and using delivery vehicles which bind activated platelets to carry active agents to the tumor while sparing surrounding normal tissue. In accordance with the present invention, then, the use of radiation to control cellular adhesion molecules involved in tumor growth is a unique approach to the treatment of neoplasms.

To determine whether radiation-induced vascular lumen localization of P-selectin was tumor type-specific or species-specific, tumors in rats, C3H mice, C57BL6 mice, and nude mice were studied. P-selectin localization to the vascular lumen was present in all tumors and all species studied. Irradiated intracranial gliomas showed P-selectin localization to the vascular lumen within one hour, whereas blood vessels in normal brain showed no P-selectin staining in the endothelium and no localization to the irradiated vascular lumen. Thus, radiation-induced localization of P-selectin to the vascular lumen is specific to the microvasculature of malignant gliomas and is not present in blood vessels of the irradiated normal brain. Radiation-induced P-selectin localization to the vascular lumen increased in time-dependent manner, until 24 hours after irradiation. Thus, the method of the present invention is contemplated to be applicable for the delivery of active agents to a broad spectrum of tumor and other neoplastic tissues.

B. Ionizing Radiation Therapy

In accordance with the present invention, ionizing radiation is used to target tissues or cells, such as neoplastic tissues or cells, for selective delivery of an active agent via a delivery vehicle comprising the active agent. Thus, the target tissues or cells are exposed to ionizing radiation, and a delivery vehicle comprising the active agent are administered before, after, during, or combinations thereof, the exposure. Examples of such ionizing radiation include, but are not limited to, gamma rays, X-rays, protons, electrons and alpha particles. Ionizing radiation is commonly used in medical radiotherapy and the specific techniques for such treatment will be apparent to one of ordinary skill in the art.

By way of particular example, the following ionizing radiation dosage ranges are utilized: about 0.1 to about 50 Gy, preferably about 2 to about 30 Gy, more preferably about 4 to about 25 Gy, and still more preferably about 10 to about 20 Gy. Particularly contemplated dosage amounts include, but are not limited to, 0.4 (or 40 cGY), 1, 2, 4, 10 and 20 Gy.

In an embodiment of the present invention contemplated to be particularly applicable to human subjects, the source of ionizing radiation comprises an external beam photon irradiation source, which is typically utilized at energy levels ranging from about 4 to about 18 MV per photon beam. Appropriate blocks, wedges, and bolus are used to deliver adequate dose to the planned target volume of target tissue. A preferred minimum source-axis distance comprises about 80 cm. The subject receives local-regional irradiation via fields that are designed to encompass sites of disease requiring palliation or primary treatment. All fields are treated daily.

Study, site, treatment intent and normal tissue considerations are also contemplated in the determination of dose. Examples of preferred dosages ranges are as follows. For an ionizing radiation dose that is administered in 1 fraction, a preferred dosage range comprises about 500 to about 1500 cGy, with a preferred dosage range comprising about 800 to about 1200 cGy. For an ionizing radiation dose that is administered in 5 fractions, a preferred dosage range comprises about 1000 to about 3000 cGy, with a preferred dosage range comprising about 1500 to about 2500 cGy, and with a more preferred dosage amount comprising about 2000 cGy. For an ionizing radiation dose that is administered in 10 fractions, a preferred dosage range comprises about 1000 to about 6000 cGy, with a preferred dosage range comprising about 2000 to about 4000 cGy, and with a more preferred dosage amount comprising about 3000 cGy.

For an ionizing radiation dose that is administered in 15 fractions, a preferred dosage range comprises about 1000 to about 7000 cGy, with a preferred dosage range comprising about 2000 to about 5000 cGy, and with a more preferred dosage amount comprising about 3500 CGy. For an ionizing radiation dose that is administered in 30 fractions, a preferred dosage range comprises about 2000 to about 12000 cGy, with a preferred dosage range comprising about 4000 to about 8000 cGy, and with a more preferred dosage amount comprising about 6000 cGy.

C. Preparation of Delivery Vehicles Comprising Active Agents

Methods for the production of the delivery vehicles comprising active agents in accordance with the present invention are described herein. For example, delivery vehicles, such as cells, peptides, proteins and antibodies, of the invention may be linked, or operatively attached, to the active agents of the invention by crosslinking or by recombinant DNA techniques.

Preferred delivery vehicles preferentially bind activated platelets. More preferably, contemplated delivery vehicles comprise proteins or peptides which bind activated platelets; antibodies which bind activated platelets; microspheres coated with proteins or peptides which bind activated platelets; liposomes conjugated to proteins or peptides which bind activated platelets, or antibodies which bind activated platelets; and combinations thereof.

Thus, preferred protein or peptide delivery vehicles preferentially bind activated platelets. Many such proteins or peptides are known in the art, and are contemplated for use in accordance with the present invention. For example, a peptide sold under the registered trademark APCITIDE® by Diatide, Inc., of Londonderry, N.H. is a peptide that binds to GPIIb/IIIa on activated platelets, as described by Taillefer J., *Nucl. Med.* 38:5 (1997). As is well-known in the art, fibrinogen preferentially binds activated platelets. Fibrinogen and apcitide thus comprise peptide delivery vehicles in accordance with the present invention.

Art-recognized bio-compatible particles, such as microspheres or liposomes, are also contemplated for use as delivery vehicles. Such particles are adapted for preferential binding to activated platelets, such as by conjugating, coating or otherwise adhering the particles with or to a peptide or antibody that preferentially binds activated platelets. For example, fibrinogen-coated microspheres (available as thrombospheres from Hemosphere, Inc., Irvine, Calif.) bind to GPIIb on activated platelets with little binding to the reticular endothelial system (RES) or other organs. These microspheres comprise preferred delivery vehicles and are conjugated to active agents in accordance with techniques described immediately below and in the Examples.

Following platelet activation, several antigens are expressed on the surface of platelets. Antibodies are conjugated to radionuclides, cytotoxic agents, gene therapy vectors and liposomes for use as delivery vehicles in accordance with the present invention. Antibody delivery vehicles may be mono-specific, bi-specific or multi-specific. That is, the antibodies may include sites which bind activated platelets and which bind an active agent, such as a gene therapy vector, preferably a viral gene therapy vector. Preferred antibodies comprise anti-P-selectin, anti-GP-IIb, and anti-GP-IIIa antibodies.

Contemplated antibodies may be polygonal antibodies but are preferably monoclonal antibodies. Preparation techniques for both polyclonal and monoclonal antibodies are well-known in the art and as such, are not discussed in detail herein. See, e.g., Kohler and Milstein, *Nature* 256:495–497 (1975); Zola, *Monoclonal Antibodies: a Manual of Techniques*, CRC Press, Inc. (1987). Further, as would be understood by one of ordinary skill in the art, the phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

While several suitable techniques for conjugating moieties to peptides and antibodies, in general, are well known in the art (see e.g., U.S. Pat. Nos. 4,340,535 and 5,776,427, and EP 44167, each of which incorporated herein by reference), certain advantages may be achieved through the application of certain preferred technology, both in the preparation of peptide and antibody delivery vehicles comprising active agents and in their purification for subsequent clinical administration. For example, while numerous types of disulfide-bond containing linkers are known which can successfully be employed to conjugate the active agent with the delivery vehicle, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the active agent prior to binding at the site of action.

In cases where a releasable active agent is contemplated, one desires to have a conjugate that will remain intact under conditions found everywhere in the body except the intended site of action, at which point it is desirable that the conjugate have good "release" characteristics. Therefore, the particular cross-linking scheme, including the particular cross-linking reagent used and the structures that are cross-linked, will be of some significance.

Cross-linking reagents are used to form molecular bridges that tie together functional groups of two different proteins (e.g., a active agent and a delivery vehicle). To link two different proteins in a step-wise manner, heterobifunctional cross-linkers can be used which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein. Useful heterobifunctional crosslinking agents include 4-succinimidyloxycarbonyl-methyl-(2-pyridyldithio)-toluene (SMPT) or N-succinimidyl-3-(2-pyridyldithio) propionate (SPDP), both of which can be obtained from Pierce, Rockland, Ill.

The spacer arm between these two reactive groups of any cross-linkers may have various length and chemical composition. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents).

An exemplary cross-linking reagent is SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to its delivery to the site of action by the binding agent. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane (Thorpe et al., *Cancer Res.* 47:5924–5931 (1987)). The use of such cross-linkers is well understood in the art.

Once conjugated, it will be important to purify the conjugate so as to remove contaminants such as unconjugated active agent or delivery vehicle. It is important to remove unconjugated delivery vehicle to reduce undesired toxicity and to avoid the possibility of competition for binding sites in the target tissue between conjugated and unconjugated species. In general, the most preferred purification technique will incorporate the use of a column matrix sold under the registered trademark BLUE-SEPHAROSE® by Pharmacia, Inc., of Piscataway, N.J. with a gel filtration or gel permeation step. The BLUE-SEPHAROSE® column matrix is a column matrix composed of a dye sold under the registered trademark CIBACRON® BLUE 3GA by Ciba Geigy Corporation of Ardsley, N.Y. and agarose, which has been found to be useful in the purification of immunoconjugates (Knowles & Thorpe, *Anal. Biochem.* 120:440–443 (1987)). The use of BLUE-SEPHAROSE® column matrix combines the properties of ion exchange with active agent binding to provide good separation of conjugated active agent from non-conjugated active agent. The BLUE-SEPHAROSE® column matrix allows the elimination of the free (non-conjugated) delivery vehicle (e.g., the antibody or fragment) from the conjugate preparation. To eliminate the free (non-conjugated) active agent a molecular exclusion chromatography step is preferred using either conventional gel filtration procedure or high performance liquid chromatography.

Alternatively, one may find that the application of recombinant DNA technology to the active agent moiety will provide additional significant benefits in accordance the invention. For example, the cloning and expression of active agent candidates, particularly toxin candidates, has now been described through the publications of others (O'Hare et al., *FEBS Lett* 210:731 (1987); Lamb et al., *Eur Jrnl Biochem* 148:265–270 (1985); Hailing et al., *Nucl Acids Res* 13:8019–8033 (1985)), it is now possible to identify and prepare smaller or otherwise variant peptides which nevertheless exhibit an appropriate active agent activity. Moreover, the use of cloned active agent candidates allows the application of site-directed mutagenesis, through which one can readily prepare and screen for mutated peptides and obtain additional useful moieties for use in connection with the present invention.

Standard recombinant DNA techniques that are well known to those of skill in the art may be utilized to express nucleic acids encoding the delivery vehicle/active agent compounds of the invention. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., *Molecular Cloning, A Laboratory Manual*, Cold Spring Harbor Laboratory, N.Y. (1989); and Ausubel et al., *Current Protocols in Molecular Biology*, Greene Publishing Associates and Wiley Interscience, N.Y. (1989).

When produced via recombinant DNA techniques such as those described herein, the delivery vehicle/active agent compounds of the invention may be referred to herein as "fusion proteins". It is to be understood that such fusion proteins contain at least a delivery vehicle and an active agent operatively attached, such that the fusion protein may be used in accordance with the methods of the present invention. The fusion proteins may also include additional peptide sequences, such as peptide spacers which operatively attach the delivery vehicle and active agent, as long as such additional sequences do not appreciably affect the delivery or active agent activities of the fusion protein.

Depending on the specific active agent used as part of the fusion protein, it may be necessary to provide a peptide spacer operatively attaching the delivery vehicle and the active agent compound which is capable of folding into a disulfide-bonded loop structure. Proteolytic cleavage within the loop would then yield a heterodimeric polypeptide wherein the delivery vehicle and the active agent compound are linked by only a single disulfide bond. See e.g., Lord et al., in *Genetically Engineered Active Agents* (Ed. A. Frank, M. Dekker Publ., p. 183) (1992). An example of such a active agent is a Ricin A-chain toxin.

When certain other active agents are utilized, a non-cleavable peptide spacer may be provided to operatively attach the delivery vehicle and the active agent of the fusion protein. Active agents which may be used in conjunction with non-cleavable peptide spacers are those which may, themselves, be converted by proteolytic cleavage, into a cytotoxic disulfide-bonded form (see e.g., Ogata et al., *J. Biol. Chem.* 256:20678–20685(1990)). An example of such an active agent is a Pseudomonas exotoxin compound.

Nucleic acids that may be utilized herein comprise nucleic acid sequences that encode a delivery vehicle of interest and nucleic acid sequences that encode a active agent of interest. Such delivery vehicle-encoding and active agent-encoding nucleic acid sequences are attached in a manner such that translation of the nucleic acid yields the delivery vehicle/active agent composition of the invention.

Standard techniques, such as those described above may be used to construct expression vectors containing the above-described nucleic acids and appropriate transcriptional/translational control sequences. A variety of host-expression vector systems may be utilized. These include but are not limited to microorganisms such as bacteria (e.g., *E. coli, B. subtilis*) transformed with recombinant bacteriophage DNA, plasmid DNA or cosmid DNA expression vectors containing delivery vehicle/active agent coding sequences; yeast (e.g., Saccharomyces, Pichia) transformed with recombinant yeast expression vectors containing delivery vehicle/active agent coding sequences; insect cell systems infected with recombinant virus expression vectors (e.g., baculovirus) containing the delivery vehicle/active agent coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the delivery vehicle/active agent coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter; lentiviral vectors).

In bacterial systems a number of expression vectors may be advantageously selected depending upon the use intended for the delivery vehicle/active agent being expressed. For example, when large quantities of delivery vehicle/active agent are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., *EMBO J* 2:1791 (1983)), in which the delivery vehicle/active agent coding sequence may be ligated individually into the vector in frame with the lac Z coding region so that a fusion protein additionally containing a portion of the lac Z product is provided; pIN vectors (Inouye et al., *Nucleic Acids Res.* 13:3101–3109 (1985); Van Heeke et al., *J. Biol. Chem.* 264:5503–5509 (1989)); and the like. pGEX vectors may also be used to express foreign polypeptides, such as the delivery vehicle/active agents as fusion proteins additionally containing glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the delivery vehicle/active agent protein of the fusion protein can be released from the GST moiety.

In an insect system, *Autograph californica* nuclear polyhidrosis virus (AcNPV) is used as a vector to express foreign genes. The virus grows in *Spodoptera frugiperda* cells. The delivery vehicle/active agent coding sequences may be cloned into non-essential regions (for example the polyhedrin gene) of the virus and placed under control of an AcNPV promoter (for example the polyhedrin promoter). Successful insertion of the delivery vehicle/active agent coding sequences will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (see e.g., Smith et al., *J. Virol.* 46:584 (1983); U.S. Pat. No. 4,215,051).

In mammalian host cells, a number of viral based expression systems may be utilized. In cases where an adenovirus is used as an expression vector, the delivery vehicle/active agent coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing delivery vehicle/active agent proteins in infected hosts (see e.g., Logan et al., *Proc. Natl. Acad. Sci. USA* 81:3655–3659 (1984)). Specific initiation signals may also be required for efficient translation of inserted delivery vehicle/active agent coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, W138, etc. For long-term, high-yield production of recombinant proteins, stable expression is preferred. For example, cell lines which stably express constructs encoding the delivery vehicle/active agent compounds may be engineered. Rather than using expression vectors which contain viral origins of replication, host cells can be transformed with delivery vehicle/active agent DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1 or 2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase (Wigler et al., *Cell* 11:223 (1977)), hypoxanthine-guanine phosphoriboxyltransferase (Szybalska et al., *Proc. Natl. Acad. Sci. USA* 48:2026 (1962)), and adenine phosphoribosyltransferase genes (Lowy et al., *Cell* 22:817 (1980)) can be employed in tk-, hgprt- or aprt-cells, respectively. Also, antimetabolite resistance can be used as the basis of selection for dhfr, which confers resistance to methotrexate (Wigler et al., *Proc. Natl. Acad. Sci. USA* 77:3567 (1980); O'Hare et al., *Proc. Natl. Acad. Sci. USA* 78:1527 (1981)); gpt, which confers resistance to mycophenolic acid (Mulligan et al., *Proc Natl Acad Sci USA* 78:2072 (1981)); neo, which confers resistance to the aminoglycoside G-418 (Colberre-Garapin et al., *J Mol Biol* 150:1 (1981)); and hygro, which confers resistance to hygromycin (Santerre et al., *Gene* 30:147 (1984)).

It is contemplated that some of the therapeutic applications of the present invention will involve the targeting of an active agent moiety to the endothelium, particularly tumor endothelium. This is due to the much greater ability of most active agents to deliver a cell killing effect as compared to other potential agents. However, there may be circumstances, such as when the target antigen does not internalize by a route consistent with efficient intoxication by delivery vehicle/active agent compounds, such as immunotoxins, where one will desire to target chemotherapeutic agents such as antitumor drugs, other cytokines, antimetabolites, alkylating agents, hormones, and the like. The advantages of these agents over their non-delivery vehicle conjugated counterparts is the added selectivity afforded by the delivery vehicle, such as an antibody. Exemplary agents include, but are not limited to, steroids, cytosine arabinoside, methotrexate, aminopterin, anthracyclines, mitomycin C, vinca alkaloids, demecolcine, etoposide, mithramycin, and the like. This list is, of course, merely exemplary in that the technology for attaching pharmaceutical agents to delivery vehicles, such as peptides or to antibodies, for specific delivery to tissues is well established.

The technology for attaching paramagnetic, radioactive and even fluorogenic ions to delivery vehicles, such as peptides and antibodies, is well established. Many of these methods involve the use of a metal chelate complex employing, for example, an organic chelating agent such a DTPA attached to the peptide or to the antibody. See e.g., U.S. Pat. No. 4,472,509. In the context of the present invention the selected ion is thus targeted to the target tissue by the delivery vehicle, such as a peptide or an antibody, allowing therapy or imaging to proceed by means of the attached ion.

A variety of chemotherapeutic and other pharmacologic agents have now been successfully conjugated to peptides and to antibodies and shown to function pharmacologically (see e.g., Vaickus et al., *Cancer Invest* 9:195–209 (1991)). Exemplary antineoplastic agents that have been investigated include doxorubicin, daunomycin, methotrexate, vinblastine, and various others. Dillman et al., *Antibody Immunocon Radiopharm* 1:65–77 (1988); Pietersz et al., *Antibody Immunoconj Radiopharm* 1:79–103 (1988). Moreover, the attachment of other agents such as neocarzinostatin (Kimura et al., *Immunogenetics* 11:373–381 (1980)), macromycin, trenimon (Ghose et al., *Meth. Enzymology* 93:280–333 (1983)) and α-amanitin has been described.

In addition to chemotherapeutic agents, the invention is contemplated to be applicable to the specific delivery of a wide variety of other agents to tumor vasculature. For example, under certain circumstances, one may desire to deliver a coagulant such as Russell's Viper Venom, activated Factor IX, activated Factor X or thrombin to the tumor vasculature. This will result in coagulation of the tumor's blood supply. One can also envisage targeting a cell surface lytic agent such as phospholipase C, (Flickinger & Trost, *Eu. J. Cancer* 12(2):159–60 (1976)) or cobra venom factor (CVF) (Vogel & Muller-Eberhard, *Anal. Biochem* 118(2):262–268 (1981))which should lyse the tumor endothelial cells directly. The operative attachment of such structures to delivery vehicles, such as peptides and antibodies, may be readily accomplished, for example, by protein-protein coupling agents such as SMPT. Moreover, one may desire to use growth factors, other cytokines or even bacterial endotoxin or the lipid A moiety of bacterial endotoxin as active agents, in order, e.g., to achieve modulation of cytokine release. The attachment of such substances to peptide and antibody delivery vehicles is again well within the skill in the art as exemplified by Ghose et al., *CRC Critical Reviews in Therapeutic Drug Carrier Systems* 3:262–359 (1987).

Thus, it is generally believed to be possible to conjugate to peptides and antibodies any active agent that has a primary or secondary amine group, hydrazide or hydrazine group, carboxyl alcohol, phosphate, or alkylating group available for binding or cross-linking to the amino acids or carbohydrate groups of the peptide or antibody. In the case of protein structures, this is most readily achieved by means of a cross linking agent as described above. In the case of doxorubicin and daunomycin, attachment may be achieved by means of an acid labile acyl hydrazone or cis aconityl linkage between the drug and the peptide or antibody. Finally, in the case of methotrexate or aminopterin, attachment is achieved through a peptide spacer such as L-Leu-L-Ala-L-Leu-L-Ala (SEQ ID NO: 1), between the y-carboxyl group of the drug and an amino acid of the peptide or antibody.

Alternatively, any such structures which are nucleic acid-encoded structures may be operatively attached to the delivery vehicles of the invention by standard recombinant DNA techniques, such as, for example, those discussed above.

In accordance with another embodiment of the present invention, platelets are used as delivery vehicles for the selective delivery of active agents to a target tissue in a vertebrate subject. Platelets are loaded or labeled with an active agent or agents in accordance with art-recognized techniques, such as those described in U.S. Pat. Nos. 5,292,524 and 5,328,840, the entire contents of each of which herein incorporated by reference. Other techniques, including electroporation, for loading or labeling platelets for use in accordance with the present invention are described in the Examples presented herein below.

As used herein, the term "loading" refers to the incorporation of material inside a delivery vehicle, such as a platelet. The incorporated material can be located, for example, within the cytoplasm of the platelet or be compartmentalized within a vacuole or organelle. The material can be taken up or "loaded" into the platelet by a variety of processes, such as, for example, phagocytosis, membrane fusion or receptor-mediated endocytosis. The pathway by which material is taken up is not critical so long as the material to be incorporated inside a platelet successfully crosses the platelet cell membrane. As would be apparent to one of ordinary skill in the art, active agents can be loaded directly into platelets or can be loaded via a loading vehicle, such as a liposome or hapten.

As disclosed in the Examples presented herein below, leukocytes bind activated platelets, and as such, are contemplated for use as delivery vehicles in accordance with the present invention. Leukocytes are loaded with active agent using the techniques described above with respect to the conjugation of active agents to peptide and antibody delivery vehicles and with respect to the loading of platelets, by electroporation or by phagocytosis, membrane fusion or receptor-mediated endocytosis. For example, leukocytes can be loaded by conjugating with a viral gene therapy vector to a platelet binding P-selectin counter receptor (PGSL) on the surface of the leukocyte using the conjugation techniques disclosed herein above.

D. Active Agents

As described hereinabove, the active agent can comprise a therapeutic or an imaging agent. The therapeutic agent can comprise chemotherapeutic agents, toxins, radiotherapeutics, or radiosensitizing agents. Each agent is loaded in a total amount effective to accomplish the desired result in the target tissue, whether the desired result be imaging the target tissue or treating the target tissue.

Chemotherapeutics useful as active agents in loaded platelets are typically small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Exemplary chemotherapeutic agents include, but are not limited to, anti-tumor drugs, cytokines, anti-metabolites, alkylating agents, hormones, and the like.

Additional examples of chemotherapeutics include common cytotoxic or cytostatic drugs such as for example: methotrexate (amethopterin), doxorubicin (adrimycin), daunorubicin, cytosine arabinoside, etoposide, 5–4 fluorouracil, melphalan, chlorambucil, and other nitrogen mustards (e.g. cyclophosphamide), cis-platinum, vindesine (and other vinca alkaloids), mitomycin and bleomycin. Other chemotherapeutics include: purothionin (barley flour oligopeptide), macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin and the like. Certainly, the use of combinations of chemotherapeutic agents is also contemplated in accordance with the present invention.

Toxins are useful as active agents. When a toxin is loaded into a platelet, the toxin-loaded platelet is specifically delivered to a target tissue by way of exposure of the target tissue to ionizing radiation, and the toxin moiety kills cells in the tissue. Toxins are generally complex toxic products of various organisms including bacteria, plants, etc.

Exemplary toxins include, but are not limited to, coagulants such as Russell's Viper Venom, activated Factor IX, activated Factor X or thrombin; and cell surface lytic agents such as phospholipase C, (Flickinger & Trost, *Eu. J. Cancer* 12(2):159–60 (1976)) or cobra venom factor (CVF) (Vogel & Muller-Eberhard, *Anal. Biochem* 118(2):262–268 (1981)) which should lyse neoplastic cells directly. Additional examples of toxins include but are not limited to: ricin, ricin A chain (ricin toxin), Pseudomonas exotoxin (PE), diphtheria toxin (DT), bovine pancreatic ribonuclease (BPR), pokeweed antiviral protein (PAP), abrin, abrin A chain (abrin toxin), gelonin (GEL), saporin (SAP), modeccin, viscumin and volkensin.

Exemplary radiotherapeutic agents include, but are not limited to, $^{47}$Sc, $^{67}$Cu $^{90}$Y, $^{109}$Pd, $^{123}$I, $^{125}$I, $^{131}$I, $^{111}$In, $^{186}$Re, $^{188}$Re, $^{199}$Au, $^{211}$At, $^{212}$Pb and $^{212}$Bi. Other radionuclides which have been used by those having ordinary skill in the art include: $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{43}$Pr, $^{161}$Tb, $^{177}$Lu, $^{191}$Os, $^{193M}$Pt, $^{197}$Hg, all beta negative and/or auger emitters. Some preferred radionuclides include: $^{90}$Y, $^{131}$I, $^{211}$At and $^{212}$Pb/$^{212}$Bi.

Radiosensitizing agents are substances that increase the sensitivity of cells to radiation. Exemplary radiosensitizing agents include, but are not limited to, nitroimidazoles, metronidazole and misonidazole (see DeVita, V. T. Jr. in *Harrison's Principles of Internal Medicine*, p.68, McGraw-Hill Book Co., N.Y. 1983, which is incorporated herein by reference), as well as art-recognized boron-neutron capture and uranium capture systems. See, e.g., Gabe, D. *Radiotherapy & Oncology* 30:199–205 (1994); Hainfeld, *J. Proc. Natl. Acad. Sci. USA* 89:11064–11068 (1992). A delivery vehicle comprising a radiosensitizing agent as the active moiety is administered and localizes at the target tissue. Upon exposure of the tissue to radiation, the radiosensitizing agent is "excited" and causes the death of the cell.

Radiosensitizing agents are also substances which become more toxic to a cell after exposure of the cell to ionizing radiation. In this case, DNA protein kinase (PK) inhibitors, such as R106 and R116 (ICOS, Inc.); tyrosine kinase inhibitors, such as SU5416 and SU6668 (Sugen Inc.); and inhibitors of DNA repair enzymes comprise contemplated examples.

Another contemplated radiosensitizing agent comprises a genetic construct which comprises an enhancer-promoter region which is responsive to radiation, and at least one structural gene whose expression is controlled by the enhancer-promoter. In accordance with the present invention, methods of destroying, altering, or inactivating cells in target tissue by delivering the genetic constructs to the cells of the tissues via delivery vehicles and inducing expression of the structural gene or genes in the construct by exposing the tissues to ionizing radiation are also contemplated. Such genetic constructs are loaded, conjugated or otherwise linked with a delivery vehicle in accordance with art-recognized techniques, such as electroporation and as are described herein above. Exemplary genetic constructs and related techniques are described in U.S. Pat. Nos. 5,817,636; 5,770,581; 5,641,755; and 5,612,318, the entire contents of each of which herein incorporated by reference. Additionally, the recombinant DNA techniques described hereinabove are contemplated to be applicable to the preparation of genetic construct active agents.

Exemplary imaging agents include, but are not limited to, paramagnetic, radioactive and fluorogenic ions. Preferably, the imaging agent comprises a radioactive imaging agent. Exemplary radioactive imaging agents include, but are not limited to, gamma-emitters, positron-emitters and x-ray-emitters. Particularly contemplated radioactive imaging agents include, but are not limited to, $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87m}$Sr, $^{99m}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb and $^{206}$Bi. Other radioactive imaging agents known by one skilled in the art can be used as well.

D. Dosages for Active Agents

Because delivery vehicles are specifically targeted to irradiated cells, a delivery vehicle which comprises an active agent is administered in a dose less than that which is used when the active agent is administered directly to a subject, preferably in doses that contain up to about 100 times less active agent. In some embodiments, delivery vehicles which comprise an active agent are administered in doses that contain about 10 to about 100 times less active agent as an active moiety than the dosage of active agent administered directly. To determine the appropriate dose, the amount of compound is preferably measured in moles instead of by weight. In that way, the variable weight of delivery vehicles does not affect the calculation. A one to one ratio of delivery vehicle to active agent in the delivery vehicles of the present invention is presumed.

Typically, chemotherapeutic conjugates are administered intravenously in multiple divided doses. Up to 20 gm IV/dose of methotrexate is typically administered. When methotrexate is administered as the active moiety in a delivery vehicle of the invention, there is about a 10- to 100-fold dose reduction. Thus, presuming each delivery vehicle includes one molecule of methotrexate to one mole of delivery vehicle, of the total amount of delivery vehicle active agent administered, up to about 0.2 to about 2.0 g of methotrexate is present and therefore administered. In some embodiments, of the total amount of delivery vehicle/active agent administered, up to about 200 mg to about 2 g of methotrexate is present and therefore administered.

By way of further example, doxorubicin and daunorubicin each weigh about 535. Presuming each delivery vehicle includes one molecule of doxorubicin or daunorubicin to one delivery vehicle, a contemplated dose range for delivery vehicle-doxorubicin vehicle or delivery vehicle-daunorubicin is between about 40 to about4000 mg. In some embodiments, dosages of about 100 to about 1000 mg of delivery vehicle-doxorubicin or delivery vehicle-daunorubicin are administered. In some embodiments, dosages of about 200 to about 600 mg of delivery vehicle-doxorubicin or delivery vehicle-daunorubicin are administered.

Toxin-containing loaded delivery vehicles are formulated for intravenous administration. Using an intravenous approach, up to 6 nanomoles/kg of body weight of toxin alone have been administered as a single dose with marked therapeutic effects in patients with melanoma (Spitler L. E., et al. (1987) *Cancer Res.* 47:1717). In some embodiments of the present invention, then, up to about 11 micrograms of delivery vehicle-toxin/kg of body weight may be administered for therapy.

The molecular weight of ricin toxin A chain is 32,000. Thus, for example, presuming each delivery vehicle includes one molecule of ricin toxin A chain to one delivery vehicle, delivery vehicles comprising ricin toxin A chain are administered in doses in which the proportion by weight of ricin toxin A chain is about 1 to about 500 $\mu$g of the total weight of the administered dose. In some preferred embodiments, delivery vehicles comprising ricin toxin A chain are administered in doses in which the proportion by weight of ricin toxin A chain is about 10 to about 100 $\mu$g of the total weight of the administered dose. In some preferred embodiments, delivery vehicles comprising ricin toxin A chain are administered in doses in which the proportion by weight of ricin toxin A chain is about 2 to about 50 $\mu$g of the total weight of the administered dose.

The molecular weight of diphtheria toxin A chain is 66,600. Thus, presuming each delivery vehicle includes one molecule of diphtheria toxin A chain to one delivery vehicle, delivery vehicles comprising diphtheria toxin A chain are administered in doses in which the proportion by weight of diphtheria toxin A chain is about 1 to about 500 $\mu$g of the total weight of the administered dose. In some preferred embodiments, delivery vehicles comprising diphtheria toxin A chain are administered in doses in which the proportion by weight of diphtheria toxin A chain is about 10 to about 100 $\mu$g of the total weight of the administered dose. In some preferred embodiments, delivery vehicles comprising diphtheria toxin A chain are administered in doses in which the proportion by weight of diphtheria toxin A chain is about 40 to about 80 $\mu$g of the total weight of the administered dose.

The molecular weight of Pseudomonas exotoxin is 22,000. Thus, presuming each delivery vehicle includes one molecule of Pseudomonas exotoxin to one delivery vehicle, delivery vehicles comprising Pseudomonas exotoxin are administered in doses in which the proportion by weight of Pseudomonas exotoxin is about 0.01 to about 100 $\mu$g of the total weight of the loaded delivery vehicle-exotoxin administered. In some preferred embodiments, delivery vehicles comprising Pseudomonas exotoxin are administered in doses in which the proportion by weight of Pseudomonas exotoxin is about 0.1 to about 10 $\mu$g of the total weight of the administered dose. In some preferred embodiments, delivery vehicles comprising Pseudomonas exotoxin are administered in doses in which the proportion by weight of Pseudomonas exotoxin is about 0.3 to about 2.2 $\mu$g of the total weight of the administered dose.

To dose delivery vehicles comprising radioisotopes in pharmaceutical compositions useful as imaging agents, it is presumed that each delivery vehicle is loaded with one radioactive active moiety. The amount of radioisotope to be administered is dependent upon the radioisotope. Those having ordinary skill in the art can readily formulate the amount of delivery vehicle-imaging agent to be administered based upon the specific activity and energy of a given radionuclide used as an active moiety. Typically about 0.1 to about 100 millicuries per dose of imaging agent, preferably about 1 to about 10 millicuries, most often about 2 to about 5 millicuries are administered.

Thus, pharmaceutical compositions contemplated to be useful imaging agents comprise delivery vehicles comprising a radioactive moiety in an amount ranging from about 0.1 to about 100 millicuries, in some embodiments preferably about 1 to about 10 millicuries, in some embodiments preferably about 2 to about 5 millicuries, in some embodiments more preferably about 1 to about 5 millicuries.

Examples of dosages include: $^{131}$I=between about 0.1 to about 100 millicuries per dose, in some embodiments preferably about 1 to about 10 millicuries, in some embodiments about 2 to about 5 millicuries, and in some embodiments about 4 millicuries; $^{111}$In=between about 0.1 to about 100 millicuries per dose, in some embodiments preferably about 1 to about 10 millicuries, in some embodiments about 1 to about 5 millicuries, and in some embodiments about 2 millicuries, $^{99m}$Tc=between about 0.1 to about 100 millicuries per dose, in some embodiments preferably about 5 to about 75 millicuries, in some embodiments about 10 to about 50 millicuries, and in some embodiments about 27 millicuries.

Depending upon the specific activity of the radioactive moiety and the weight of the delivery vehicle, the dosage defined by weight varies. For example, in a pharmaceutical composition comprising an $^{131}$I-loaded platelet in which the specific activity of $^{131}$I-loaded platelet is about 2000 Ci/mmol, administering the dose of about 0.1 to about 100 millicuries is the equivalent of 0.1 to about 100 $\mu$g $^{131}$I-loaded platelet, administering the dose of about 1 to about 10 millicuries is the equivalent of about 1 to about 10 $\mu$g of $^{131}$I-loaded platelet, administering the dose of about 2 to about 5 millicuries is equivalent to giving about 2 to about 5 $\mu$g of $^{131}$I-loaded platelet and administering the dose of about 1 to about 5 millicuries is equivalent to giving about 1 to about 5 $\mu$g of $^{131}$I-loaded platelet.

In a pharmaceutical composition comprising a loaded platelet comprising a single $^{111}$In in which the specific activity of $^{111}$In-loaded platelet is about 1 Ci/mmol, administering the dose of about 0.1 to about 100 millicuries is the equivalent of about 0.2 to about 200 mg $^{111}$In-loaded platelet, administering the dose of about 1 to about 10 millicuries is the equivalent of about 2 to about 20 mg of $^{111}$In-loaded platelet, administering the dose of about 2 to about 5 millicuries is equivalent to giving about 4 to about 10 mg of $^{111}$In-loaded platelet and administering the dose of about 1 to about 5 millicuries is equivalent to giving about 2 to about 10 mg of $^{111}$In-loaded platelet.

To load delivery vehicles with radioisotopes in pharmaceutical compositions useful as therapeutic agents, it is presumed that each delivery vehicle is loaded with one radioactive active moiety. The amount of radioisotope to be administered is dependent upon the radioisotope. Those having ordinary skill in the art can readily formulate the amount of delivery vehicle-radio-therapeutic agent to be administered based upon the specific activity and energy of a given radionuclide used as an active moiety. For therapeutics that comprise $^{131}$I, between about 10 to about 1000 nanomoles (nM), preferably about 50 to about 500 nM, more preferably about 300 nM of $^{131}$I at the tumor, per gram of tumor, is desirable. Thus, if there is about 1 gram of tumor, and about 0.1% of the administered dose is delivered to the tumor, about 0.5 to about 100 mg of $^{131}$I-delivery vehicle is administered. In some embodiments, about 1 to about 50 mg of $^{131}$I-delivery vehicle is administered. In some embodiments, about 5 to about 10 mg of $^{131}$I-delivery vehicle is administered. Wessels B. W. and R. D. Rogus (1984) *Med. Phys.* 11:638 and Kwok, C. S. et al. (1985) *Med. Phys.* 12:405, both of which are incorporated herein by reference, disclose detailed dose calculations for diagnostic and therapeutic vehicles which may be used in the preparation of pharmaceutical compositions of the present invention which include radioactive delivery vehicles.

E. Pharmaceutical Compositions

After a sufficiently purified delivery vehicle comprising active agent has been prepared, one will desire to prepare it into a pharmaceutical composition that may be administered in any suitable manner. Preferred administration techniques include parenteral administration, intravenous administration and infusion directly into a target tissue, such as a solid tumor or other neoplastic tissue. This is done by using for the last purification step a medium with a suitable pharmaceutical composition.

Suitable pharmaceutical compositions in accordance with the invention will generally comprise an amount of the desired delivery vehicle-active agent in accordance with the dosage information set forth above admixed with an acceptable pharmaceutical diluent or excipient, such as a sterile aqueous solution, to give an appropriate final concentration in accordance with the dosage information set forth above with respect to the active agent. Such formulations will typically include buffers such as phosphate buffered saline (PBS), or additional additives such as pharmaceutical excipients, stabilizing agents such as BSA or HSA, or salts such as sodium chloride.

For parenteral administration it is generally desirable to further render such compositions pharmaceutically acceptable by insuring their sterility, non-immunogenicity and non-pyrogenicity. Such techniques are generally well known in the art as exemplified by *Remington's Pharmaceutical Sciences,* 16th Ed. Mack Publishing Company (1980), incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

F. Therapeutic Methods

A therapeutic method is contemplated in accordance with the present invention. The method pertains to the delivery of an active agent to a target tissue in a vertebrate subject, and comprises: (a) exposing the target tissue to ionizing radiation; and (b) administering a delivery vehicle to the vertebrate subject before; after; during; before and after; before and during; during or after; or before, during and after exposing the target tissue to the ionizing radiation. Indeed, any combination of administering a delivery vehicle to the vertebrate subject before, during and/or after exposing the target tissue to the ionizing radiation is contemplated to fall within the scope of the present invention. The delivery vehicle comprises the therapeutic agent, and delivers the agent to the target tissue.

The target tissue is exposed to ionizing radiation in the amounts and ranges discussed herein. A preferred minimal dose of ionizing radiation comprises about 400 cGy. A more preferred dose comprises about 10 Gy, in that maximal platelet aggregation has been observed at this dosage level. Platelet aggregates are typically first observed in the target tissue one hour after irradiation and maximal platelet aggregation in target tissue is typically observed at about 24 hours after irradiation. After about 48 hours after irradiation, platelet aggregates begin to diminish.

In a preferred schedule of administration, delivery vehicles comprising the active agent are administered about one hour prior to irradiation or about ten minutes after irradiation. Applicant has observed that radiation induced platelet aggregation increased three-fold over untreated controls when delivery vehicles were administered about ten minutes after administration. When delivery vehicles were administered prior to irradiation, a ten-fold increase in platelet aggregation in tumors as compared to untreated controls was observed.

Optionally, delivery vehicles comprising the active agent are administered both about one hour prior to irradiation and about ten minutes after irradiation. Of course, dosage levels of the active agent are adjusted to reflect two administrations of the delivery vehicles comprising the active agent.

In a preferred embodiment of a therapeutic method of the present invention, the target tissue comprises a neoplasm. As described hereinabove, it is contemplated that any neoplasm can be selectively targeted for delivery of a therapeutic agent in accordance with the method of the present invention.

Warm-blooded vertebrates comprise particularly contemplated subjects for treatment in accordance with the methods of the present invention. Therefore, the invention concerns mammals and birds.

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

A suitable therapeutic agent comprises any agent having a therapeutic effect, including but not limited to chemotherapeutics, toxins, radiotherapeutics, or radiosensitizing agents. Particularly contemplated chemotherapeutics, toxins, radiotherapeutics, or radiosensitizing agents are set forth in detail above. Preferably, the therapeutic agent is administered in a pharmaceutically acceptable form comprising an effective amount of the desired therapeutic agent-delivery vehicle, as provided in accordance with the dosage information set forth above.

When the therapeutic agent is a radiosensitizing agent the method further comprises the step of again exposing the target tissue to ionizing radiation after delivery of the radiosensitizing agent-loaded delivery vehicles to the target tissue. Preferably, the target tissue is exposed to ionizing radiation at a time point of about 6 hours after the initial irradiation of the target tissue.

By way of further explanation, pharmacokinetic and pharmacodynamic studies were performed by studying the time course of radiolabeled delivery vehicles in various tissues, including tumor, liver, spleen and heart. Each region of interest was studied by measuring counts per pixel in each of the regions. Using $^{111}$In as a label, the time point for maximal localization in tumors was about 6 hours after initial tissue irradiation in accordance with the present invention. At about 24 hours after initial irradiation, increased platelet aggregation in tumors was observed; but, a concurrent increase in the platelet aggregation in liver, spleen and heart was observed. As would be apparent to one of ordinary skill in the art, the elucidation of these pharmacodynamic parameters facilitates the timing of a second dose of ionizing radiation to the target tissue, after a radiosensitizing agent has been delivered to the target tissue, so that desired therapeutic effects in the target tissue are maximized and undesired negative effects in other tissues are minimized.

G. Treatment of Angiogenesis

Angiogenesis, or the growth of new blood vessels, is an essential component to the growth of tumors (Folkman, J., *N Engl J Med* 28;333(26), 1757–1763 (1995)). These newly proliferating blood vessels have distinct expression of cell adhesion molecules (Wu et al., *British Journal of Cancer* 68, 883–9 (1994)). P-selectin is one of many cell adhesion molecules expressed on the endothelium of angiogenic blood vessels (Brooks, P. C., *Cancer Metastasis Rev.* 15:187–194 (1996)).

In view of the relationship between P-selectin expression and platelet aggregation disclosed herein, a therapeutic method pertaining to the inhibition of angiogenesis is contemplated in accordance with the present invention. The present invention thus provides for a method for the inhibition of angiogenesis in a tissue, and thereby modulating events in the tissue which depend upon angiogenesis. Such a method particularly involves the exposure of a target tissue undergoing angiogenesis to ionizing radiation in conjunction with the administration of a delivery vehicle comprising a therapeutic agent, whereby the delivery vehicle is selectively delivered to the blood vessels and angiogenesis in the blood vessels is inhibited. Indeed, angiogenic blood vessels are contemplated "target tissues", as the term is used herein. Any therapeutic agent as characterized herein and/or that has an inhibitory effect on angiogenesis is contemplated for use in the method. Such agents may be referred to as "antiangiogenic agents". Particularly contemplated therapeutic agents include coagulants and radiotherapeutics, as are more fully described herein above.

Angiogenesis includes a variety of processes involving neovascularization of a tissue including "sprouting", vasculogenesis, or vessel enlargement. With the exception of traumatic wound healing, corpus luteum formation and embryogenesis, it is believed that the majority of angiogenesis processes are associated with disease processes.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, capillary proliferation in atherosclerotic plaques and osteoporosis, and cancer associated disorders, such as solid tumors, solid tumor metastases, angiofibromas, retrolental fibroplasia, hemangiomas, Karposi's sarcoma and the like cancers which require neovascularization to support tumor growth.

Thus, methods which inhibit angiogenesis in a diseased tissue ameliorates symptoms of the disease and, depending upon the disease, can contribute to cure of the disease. In one embodiment, the invention contemplates inhibition of angiogenesis, per se, in a tissue. The extent of angiogenesis in a tissue, and therefore the extent of inhibition achieved by the present methods, can be evaluated by a variety of methods, such as the chick chorioallantoic membrane assay. The chick chorioallantoic membrane assay has be described in detail by others, and further has been used to measure both angiogenesis and neovascularization of tumor tissues. See Ausprunk et al., *Am. J. Pathol.*, 79:597–618 (1975); Ossonski et al., *Cancer Res.*, 40:2300–2309 (1980); and U.S. Pat. No. 5,753,230, the entire contents of each of which herein incorporated by reference.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

Thus, in one related embodiment, a tissue to be treated is an inflamed tissue and the angiogenesis to be inhibited is inflamed tissue angiogenesis where there is neovascularization of inflamed tissue. In this case the method contemplates inhibition of angiogenesis in arthritic tissues, such as in a patient with chronic articular rheumatism, in immune or non-immune inflamed tissues, in psoriatic tissue and the like.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a hemangioma or angiofibroma and the like cancer, and the angiogenesis to be inhibited is tumor tissue angiogenesis where there is neovascularization of a tumor tissue.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor. Stated differently, the present invention provides for a method of modulating tumor neovascularization by modulating tumor angiogenesis according to the present methods. Similarly, the invention provides a method of modulating tumor growth by practicing the angiogenesis-modulating methods.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

H. Imaging Techniques

A diagnostic imaging method is contemplated in accordance with the present invention. The method pertains to the delivery of an imaging agent to a target tissue in a vertebrate subject, and comprises: (a) exposing the target tissue to ionizing radiation; (b) administering a delivery vehicle to the vertebrate subject before, after, during, or combinations thereof, exposing the target tissue to the ionizing radiation; and (c) detecting the imaging agent in the target tissue. The delivery vehicle comprises an imaging agent, and aggregates in the target tissue to thereby deliver the agent to the target tissue so that the imaging agent can be detected.

In a preferred embodiment of a diagnostic imaging method of the present invention, the target tissue comprises a neoplasm. As described hereinabove, it is contemplated that any neoplasm can be selectively targeted for delivery of an imaging agent in accordance with the method of the present invention.

According to the imaging method of present invention, imaging agents are useful in diagnostic procedures as well as in procedures used to identify the location of cells of a target tissue, such as metastasized neoplastic cells. Imaging can be performed by many procedures well-known to those having ordinary skill in the art and the appropriate imaging agent useful in such procedures and as are described in detail herein above may be loaded in delivery vehicles as also described in detail herein. Imaging can be performed, for example, by radioscintigraphy, nuclear magnetic resonance imaging (MRI) or computed tomography (CT scan). The most commonly employed radionuclide imaging agents include radioactive iodine and indium.

Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium.

The following Laboratory Examples have been included to illustrate preferred modes of the invention. Certain aspects of the following Laboratory Examples are described in terms of techniques and procedures found or contemplated by the present inventor to work well in the practice of the invention. These Laboratory Examples are exemplified through the use of standard laboratory practices of the inventor. In light of the present disclosure and the general level of skill in the art, those of skill will appreciate that the following Laboratory Examples are intended to be exemplary only and that numerous changes, modifications and alterations can be employed without departing from the spirit and scope of the invention.

EXAMPLE 1

P-selectin Accumulation in the Lumen of Irradiated Blood Vessels

Ionizing radiation induces the inflammatory response in part through leukocyte binding to cell adhesion molecules that are expressed on the vascular endothelium. The effects of x-irradiation on the pattern of immunohistochemical staining of CD62P (P-selectin) was studied. P-selectin was localized within cytoplasmic granules in the untreated vascular endothelium. P-selectin immunohistochemical staining was observed at the luminal surface of vascular endothelium within one hour of irradiation. Increased P-selectin staining at the blood tissue interface occurred primarily in pulmonary and intestinal blood vessels.

To determine whether P-selectin localization at the vascular lumen occurs through exocytosis of endothelial cells stores in addition to platelet aggregation, the vascular endothelium from the circulation were removed and endothelial cells were irradiated in vitro. The mechanisms by which ionizing radiation induced translocation of P-selectin were studied by using immunofluorescence of human umbilical vein endothelial cells (HUVEC) and confocal microscopy. Prior to irradiation, P-selectin is localized in cytoplasmic reservoirs of HUVEC. Following irradiation of HUVEC, P-selectin was translocated to the cell membrane, where it remained tethered. The threshold dose required for translocation of P-selectin to the cell membrane was 2 Gy.

To determine whether P-selectin in Weibel-Palade bodies requires microtubule-dependent membrane transport, microtubule depolymerizing agents, colcemid and nocodozol, were added. Microtubule-depolymerizing agents prevented radiation-induced P-selectin translocation to the cell membrane. Thus, P-selectin accumulates in irradiated blood vessels through both platelet aggregation and microtubule dependent exocytosis of storage reservoirs within the vascular endothelium.

MATERIALS AND METHODS

Cell lines. Human umbilical vein endothelial cell (HUVEC) cultures were prepared from fresh (<24-hour-old) human umbilical veins transported to the laboratory in sterile buffer at 4° C. as described by Hallahan et al., *Biochemical & Biophysical Research Communications* 217:784–795 (1995) and by Hallahan et al., *Cancer Research* 56:5150–5155 (1996). The vein was cannulated, filled with 0.2% collagenase, and incubated at 37° C. for 15 minutes. Cells were flushed and complete medium was added, followed by centrifugation at 2000 rpm for 5 min. The cell pellet was resuspended and maintained in M199 with 10% fetal calf serum, 10% human serum, and pen/strep/amphotericin B solution (Sigma) on gelatin-coated (0.2%) tissue culture dishes at 37° C. in 5% $CO_2$. The purity of endothelial cell cultures was verified by staining for factor VIII. Confluent cells were harvested with 0.1% collagenase 0.01% EDTA and subcultured at a ratio of 1:3. HUVECs were used at third passage; this reduced the number of passenger cells and allowed for uniform expression of cellular adhesion molecules. Thrombin was purchased from Sigma.

Immunofluorescence microscopy of P-selectin in endothelial cells. Primary-culture vascular endothelial cells were grown to 80% confluence on glass slides. During inhibition experiments, HUVEC were incubated with colcemid (500 nM) or nocodozol (500 nM) for 20 minutes prior to irradiation. Cytochalazin-B (1 mM) was added for 60 minutes before irradiation. Cells were treated with either thrombin or gamma irradiation from a $^{60}Co$ source (GAMMACELL™ 220) as described by Hallahan, D. E. et al., *Biochemical & Biophysical Research Communications* 217:784–795 (1995) and by Hallahan, D. E. et al., *Cancer Research* 56:5150–5155 (1996). After treatment, HUVEC were fixed with 4% paraformaldehyde for 10 min at room temperature, washed 3 times with antibody buffer (4 gm bovine serum albumin, 0.1 gm sodium azide, 0.75 gm glycine, and 100 $\mu$l PBS) and 2 times in Hanks salt solution. Non-specific binding of antibody was blocked with 50% goat serum for 30 min at 37° C. in a humid chamber.

Cells were then washed with antibody buffer and Hanks salt solution and incubated with 100 $\mu$l of 10 $\mu$g/mL anti-P-selectin primary antibody (Pharmingen, catalog #09361A, rabbit anti-human) for 2 to 3 hours at 37° C. in a humid chamber. Cells were then washed with antibody buffers and Hanks solution and incubated with 10 $\mu$l of a 1:300 dilution of FITC conjugated goat anti-rabbit IgG (cat. #L42001) for 30 min. Cells were washed, counterstained with DAPI, and mounted with anti-fade mounting medium. After washings, cells were visualized with a Zeiss Photomicroscope III fluorescence microscope for incident-light excitation. Slides were mounted and examined for fluorescence and by phase microscopy.

Using images of cells from a 100X objective using confocal microscopy, fluorescence intensity was measured, in pixels, on the cell membrane. Fluorescence intensity was measured by NIH Image software as described by Hallahan, D. E. and Virudachalam, S., Proc. Natl. Acad. Sci. USA 94:6432–7 (1997). Ten randomly selected cells were imaged. Experiments were performed 3 to 4 times. All data were analyzed by use of CHI SQUARE STATISTICA™ for WINDOWS® software (StatSoft, Inc., Tulsa, Okla.).

Irradiation of mice. C57BL6 Mice (Jackson Laboratories) were irradiated as described by Hallahan, D. E. and Virudachalam, S., Cancer Research 57, 2096–2099 (1997) and by Hallahan, D. E. and Virudachalam, S., Proc. Natl. Acad. Sci. USA 94:6432–7 (1997). Briefly, mice were immobilized in a lucite tube. Lead was shaped over the abdomen during thoracic irradiation and over the thorax during abdominal irradiation. The chest or abdomen were irradiated with 10 Gy at the rate of 2 Gy per minute losing 150 kv x-rays from a General Electric MAXITRON™ generator. Ten, 30, 60, or 120 minutes after irradiation, mice were euthanized by intraperitoneal injection of xylazine and ketamine. Tissues were fixed in formalin and embedded in paraffin. Tissue blocks were then sectioned in 5 $\mu$m thick sections.

Immunohistochemistry. Tissue sections were baked at 60° C. for 1 hour, cleared in xylene, and hydrated through a descending alcohol series to distilled water. For P-selectin and CD45 immunostaining, the hydrated sections were incubated with Protease I (Ventana Biotech, Tucson, Ariz.) for 8 minutes at 42° C. For ICAM immunostaining, the hydrated sections were incubated with Protease II (Ventana Biotech) for 8 minutes at 42° C. After brief washing in ddH$_2$O, endogenous activity was blocked by treatment of the sections with 3% hydrogen peroxide in methanol for 20 min. Two tissue sections from each mouse were then incubated overnight at 4° C. at a titer of 2.5 $\mu$g/mL for anti-P-selectin antibody (Pharmingen, San Diego, Calif.). One slide from each sample was treated in a similar fashion and incubated overnight in normal serum immunoglobulin (Ventana Medical Systems, Tucson, Ariz.).

The immunohistochemical staining was performed on a Ventana GEN11™ system (Ventana Medical Systems). The Ventana GEN11™ system uses an indirect strepavidin-biotin system conjugated with horseradish peroxidase for detection of the immunocomplex and diaminobenzidine as a substrate for localization. The Ventana GEN11™ system uses a cartridge delivered avidin/biotin blocking kit to block endogenous biotin. The immunostained sections were counterstained with hematoxylin, dehydrated through an ascending alcohol series, cleared, and coverslipped. Tissue sections were imaged using 40X objective lens.

RESULTS

Localization of P-selectin to the blood-tissue interface in irradiated blood vessels. To determine whether ionizing radiation altered the immunostaining pattern of P-selectin, C57BL6 mice were treated with thoracic irradiation (10 Gy). During immunohistochemical analysis of the irradiated tissues, it was observed that P-selectin protein in the vascular endothelium was localized to the tissue-blood interface at one hour after irradiation. Prior to irradiation, P-selectin staining was localized to the endothelial cells, but it was redistributed to the tissue-blood interface within 1 hour of irradiation. Leukocytes localized with redistributed P-selectin at the blood-tissue interface in irradiated pulmonary vessels.

To determine whether P-selectin redistribution to the vascular lumen after irradiation is specific to the lung, tissue sections from irradiated small intestine and colon were studied. The irradiated small intestine showed P-selectin localized to the blood-tissue interface at one hour after irradiation. Likewise, the vascular endothelium within the irradiated large intestine showed P-selectin localized to the vascular lumen.

To study the duration of P-selectin translocation to the luminal surface of irradiated blood vessels, later time points were studied. P-selectin localization to the blood-tissue interface persisted at 6 hours after irradiation. P-selectin is also present in the granules of platelets and was therefore observed within platelet aggregates that were first observed within irradiated blood vessels at 6 hours after irradiation. At 24 hours, P-selectin immunohistochemistry revealed staining of platelet aggregates within irradiated blood vessels of the lung. Platelet aggregation was transient, and resolution began by 48 hours after irradiation. At 24 hours after irradiation, leukocytes adhered to P-selectin within platelet aggregates.

Radiation-induced P-selectin exocytosis in irradiated endothelial cells. To determine whether radiation-induced P-selectin accumulation in the vascular lumen was specific for vascular endothelium in vivo, primary-culture HUVEC were irradiated. The in vitro endothelial cell model provides a means to study direct effects of ionizing radiation on the vascular endothelium by removing platelets, leukocytes and thrombin. Immunofluorescence microscopy allowed the visualization of P-selectin in endothelial cells.

P-selectin was compartmentalized in Weibel-Palade bodies, which underwent membrane transport to the cell membrane after exposure to ionizing radiation. Prior to irradiation, P-selectin was localized to storage reservoirs within the cytoplasm of endothelial cells. At 15 minutes after irradiation (2 Gy), WPB began translocation to the cell apical membrane. Translocation of P-selectin to the cell membrane was complete at 30 min after irradiation. P-selectin remained tethered to the cell membranes at 60 minutes after exposure to 2 Gy and P-selectin immunofluorescence stained in a starry sky pattern. The increased intensity of immunofluorescence after exocytosis may be due to increased accessibility of epitopes once P-selectin is translocated to the cell membrane. P-selectin ELISA analysis of medium showed no release of P-selectin into the medium at 1, 2, 4, 6 or 24 hours after irradiation.

To determine whether radiation-induced P-selectin translocation is dose-dependent, HUVEC were treated with 1, 2 and 5 Gy. Confocal microscopy was used to measure immunofluorescence on the cell surface, which was quantified by NIH Image software. There was minimal WPB exocytosis in response to 1 Gy, but it was observed that 2 Gy was sufficient to induce P-selectin translocation to the cell membrane of endothelial cells. Higher doses induced no more rapid or efficient translocation than 2 Gy, indicating that there is minimal dose dependence in x-ray-induced P-selectin translocation.

P-selectin immunofluorescence of endothelial cells treated with microtubule depolymerizing agents. Membrane transport of storage reservoirs requires motor protein tracking over the cytoskeleton, as described by Eyden, B. P., *Journal of Submicroscopic Cytology & Pathology* 25:145–8 (1993) and by Sinha, S. and Wagner, D. D., *European Journal of Cell Biology* 43:377–83 (1987). To determine whether microtubules or actin are required for radiation-induced exocytosis of P-selectin, the microtubule depolymerizing agents, colcemid and nocodozol, or the actin antagonist cytochalasin-B were utilized. HUVEC were pretreated with these agents for 40 min followed by irradiation. Immunofluorescent confocal microscopy showed P-selectin translocation to the cell membrane of irradiated HUVEC. At 60 min following irradiation, HUVEC treated with radiation alone showed the starry sky pattern of immunofluorescence of P-selectin on the cell membrane.

The microtubule depolymerizing agents colcemid and nocodozol inhibited x-ray induced translocation of P-selectin and showed P-selectin localized to cytoplasmic storage reservoirs in a pattern similar to untreated control. Conversely, cells pretreated with cytochalasin-B showed no inhibition of P-selectin translocation. Localization of P-selectin on the cell membrane was quantified by use of immunofluorescence confocal microscopy, which was quantified by NIH Image software. This showed an 8-fold increase in P-selectin immunofluorescence on the cell surface, which was abrogated by Colcemid and nocodozol, but not the actin antagonist cytochalasin-B.

EXAMPLE 2

Absence of P-selectin Immunostaining in the Vascular Endothelium is Associated with the Attenuation of Radiation-induced Platelet Aggregation P-selectin is an adhesion molecule sequestered in storage reservoirs in platelets and vascular endothelium and rapidly undergoes exocytosis following x-irradiation. P-selectin adheres to sialylated molecules on the surface of leukocytes to slow the flow of the cells and begin leukocyte activation. To determine whether a P-selectin contributes to the radiation response, the immunohistochemical pattern of staining of P-selectin in irradiated tissues was studied. Prior to x-irradiation, P-selectin is present within the vascular endothelium. Within one to two hours, P-selectin stains along the blood-tissue interface. At four to six hours after irradiation, P-selectin staining filled the vascular lumen in a pattern consistent with platelet aggregation.

To verify that platelet aggregation was present in these irradiated blood vessels, tissue sections underwent immunohistochemical staining with anti-GPIIIa antibodies that stained platelets. No P-selectin or GPIIIa staining was found in the brain or kidney, but both P-selectin and GPIIIa staining were present in the irradiated lung, intestine and tumor vessels. The P-selectin knockout mouse was used to study platelet aggregation (i.e. GPIIIa accumulation) in the absence of P-selectin staining in the vascular endothelium. The GPIIIa staining was not localized to the lumen of irradiated blood vessels in the knockout mouse, but extravasated into the irradiated lung, and tumors. Knockout of the P-selectin gene leads to extravasation of blood components to the irradiated tissues.

MATERIALS AND METHODS

Irradiation of Mice. P-selectin knockout mice, prepared as described by Mayadas et al. *Cell* 74:541–54 (1993), were obtained from Jackson Laboratories. Mice were bred in the transgenic mouse core laboratory at Vanderbilt University, Nashville, Tenn. Five- to six-week-old mice were irradiated as described by Hallahan, D. E. and Virudachalam, S., *Cancer Research* 57:2096–2099 (1997) and by Hallahan, D. E. and Virudachalam, S., *Proc. Natl. Acad. Sci. USA* 94:6432–7 (1997). Briefly, mice were immobilized in lucite cylinders. Lead shielding was used to eliminate dose to the abdomen during thoracic irradiation. Likewise, thoracic shielding was used during abdominal irradiation. Mice were treated with 250 KV x-rays using a General Electric MAXITRON™ generator at a dose rate of 2 Gy per minute. After irradiation, mice were euthanized by intraperitoneal injection of xylazine and ketamine. Tissues were excised and analyzed for platelet aggregation at 6, 24 and 48 hours after irradiation. Tissues were fixed in formalin and embedded in paraffin.

Immunohistochemistry of Tissue Sections. Tissue sections were baked at 60° C. for 1 hour, cleared in xylene, and hydrated through a descending alcohol series to distilled water. After brief washing in distilled $H_2O$, endogenous activity was blocked by treatment of the sections with 3% hydrogen peroxide in methanol for 20 minutes. Two tissue sections from each mouse were then incubated overnight at 4° C. at a titer of 2.5 µg/mL for anti-P-selectin antibody (Pharmingen, San Diego, Calif.) or platelet antibody anti-GP-IIIa (Pharmingen, San Diego, Calif.). Increased GP-IIIa staining as compared to untreated controls determined the presence of platelet aggregation. One section from each lung was treated in a similar fashion and incubated overnight in normal serum immunoglobulin (Ventana Medical Systems, Tucson, Ariz.). The immunohistochemical staining was performed on a Ventana GEN11™ system (Ventana Medical Systems) which uses an indirect strepavidin-biotin system conjugated with horseradish peroxidase for detecting the immunocomplex and diaminobenzidine as a substrate for localization, as well as a cartridge delivered avidin/biotin blocking kit to block endogenous biotin. The immunostained sections were counterstained with eosin and hematoxylin, dehydrated through an ascending alcohol series, cleared, and coverslipped.

Immunofluorescence Staining of platelet aggregates in irradiated blood vessels. Immunofluorescence staining was performed as described by Hallahan, D. E. and Virudachalam, S., *Cancer Research* 57:2096–2099 (1997) and by Hallahan, D. E. and Virudachalam, S., *Proc. Natl. Acad. Sci. USA* 94:6432–7 (1997). Tissue sections (5 µm) were mounted on slides and labeled with anti-GP-IIIa antibodies as described above. After incubation with biotinylated secondary antibody, sections were incubated with 200 µl of Avidin-Cy3 (10 µg/mL) for 30 min in a humid chamber at room temperature. Avidin-Cy3 (Amersham), 5 µg/mL was added to 200 µL of blocking buffer and filtered through a 0.2-µm Millipore filter, before addition of the fluorochrome to slides. Coverslips were removed, and sections were washed with 4X SSC/0.1% solution of a detergent sold under the registered trademark TRITON® X by Rohm and Hass Company of Philadelphia, Pa. at room temperature. Slides were counterstained in DAPI and rinsed with 2X SSC for 10 seconds. Coverslips were then placed on slides with antifade and blotted. Immunofluorescent images were visualized with a Zeiss Photomicroscope III fluorescence microscope.

Platelet aggregation was quantified by measuring fluorescence intensity in blood vessels of tissue stained with anti-GPIIIa antibody (Pharmingen, San Diego, Calif.). Blood vessels were identified by auto-fluorescence of red blood cells using green filter. The filter was then changed to red wavelengths so that Cy3 stained platelets could be quantified. Fluorescence intensity within blood vessels measured using 40X objective microscopic images of tissues sections. Ten blood vessels in each tissue section were photographed using CCD camera. Fluorescence intensity was measured by NIH Image software as described by Hallahan, D. E. and Virudachalam, S., *Cancer Research* 57:2096–2099 (1997) and by Hallahan, D. E. and Virudachalam, S., *Proc. Natl. Acad. Sci. USA* 94:6432–7 (1997). Platelet aggregates were defined as the presence of increased GP-IIIa staining in blood vessels. The percentage of blood vessels with GP-IIIa staining was determined in 4 mice, each treated with x-rays or sham irradiation. A total of 10 vessels in each of 4 mice (40 vessels) were measured. All data were analyzed by use of Students Paired T-test.

Tumor implantation in rodents: GL-261 glioma cells were maintained in F-12/DME 50% mixture and 7% fetal calf serum, and penicillin and streptomycin. Subconfluent tumor cells were trypsinized, washed, and injected subcutaneously into the hindlimb of C57BL6 mice (Jackson Labs). Tumors were grown to 400 mm$^3$. Tumors were treated with x-irradiation using 250 kV x-rays as described by Hallahan, D. E. et al., *Nature Medicine* 1:786–791 (1995). Tumors were treated with 10 Gy at a dose rate of 1 Gy per minute.

P-selectin −/− mice were obtained from Jackson Laboratories (Bar Harbor, Me.). GL261 cells (10$^6$) were injected subcutaneously into the hindlimb of P-selectin −/− mice. Tumors were growth to a volume of 400 mm$^3$ and irradiated with 10 Gy. At 6 and 24 hours following irradiation, mice were euthanized by intraperitoneal injection of xylazine and ketamine. Tumors were fixed in formalin and embedded in paraffin. Tumors were sectioned and stained with the anti-GPIIIa antibody as described above.

RESULTS

Histologic Pattern of P-selectin Expression in Irradiated Tissues. To determine whether platelet aggregation in irradiated blood vessels was associated with WPB exocytosis, immunohistochemical analysis of P-selectin, one of the WPB components was utilized. C57BL6 mice were treated with thoracic irradiation and tissues were fixed at the indicated times. Prior to irradiation, P-selectin was localized to the vascular endothelium. Within 60 minutes of irradiation, P-selectin was localized to the blood-tissue interface. P-selectin staining extended into the vascular lumen. At 4 hours after irradiation, P-selectin in platelet aggregates was stained within these blood vessels. Platelet aggregation continued to accumulate in irradiated blood vessels over 24 hours.

Association of radiation-induced platelet aggregation with P-selectin staining. To differentiate between P-selectin in platelets and P-selectin in the endothelium, an anti-GPIIIa antibody to platelets was utilized. GPIIIa staining showed no platelet aggregation at one hour, indicating that x-ray induced intraluminal P-selectin may be of endothelial origin at this early time point. To quantify platelet aggregation, tissue sections from irradiated lungs with anti-GPIIIa antibody were stained. The percentage of irradiated blood vessels with platelet aggregates increased over time. Four hours after irradiation, 40% of blood vessels showed platelet aggregation. The percentage of pulmonary vessels with aggregates increased to 75% at 24 hours (p=0.01). Thereafter, platelet aggregation decreases.

Platelet aggregation is attenuated by antibodies to P-selectin and is markedly delayed in P-selectin −/− mice, as described by Subramaniam et al., *Blood* 87:1238–42 (1996) and by Boukerche, H., *British Journal of Haematology* 92:442–51 (1996). To determine whether P-selectin staining in the vascular endothelium is associated with platelet aggregation, the number of platelet aggregates in untreated murine blood vessels that stained positively for P-selectin were studied, as compared to tissues without P-selectin. P-selectin staining was found in large pulmonary blood vessels, but not in the pulmonary capillary endothelium. P-selectin staining was also observed in the irradiated small intestine endothelium. P-selectin staining was not observed in the irradiated brain or kidney.

To determine whether P-selectin staining was associated with radiation-induced platelet aggregation, platelets were quantified using anti-GPIIIa antibody and immunofluorescence. The brain, lung, kidney, small intestine and large intestine were each irradiated and tissues were excised at 24 h after irradiation. Platelet aggregation in irradiated blood vessels was quantified by GPIIIa immunothoracense. Tissues with no P-selectin staining showed an increase in GP-IIIa staining in 8% (brain) and 5% (kidney) as compared to tissues with P-selectin staining in the endothelium 75% (lung), 85% (small intestine) and 88% (large intestine)(p=0.002). Moreover, the pulmonary microvascular endothelium did not contain P-selectin and did not show platelet aggregation.

Absence of radiation induced platelet aggregation in blood vessels of P-selectin −/− mice. To determine whether P-selectin is required for radiation-induced platelet aggregation, P-selectin knockout mice were irradiated and stained for platelets utilizing the platelet antibody anti-GP IIIa. Marked attenuation of platelet aggregation in intestines of irradiated P-selectin knockout mice. Immunohistochemical staining for platelet antigens was utilized to measure of the difference in platelet aggregation in the P-selectin knockout mouse as compared to the P-selectin +/+ mouse. FACS analysis of platelets was performed by use of anti-GPIIIa antibody staining of washed blood components and showed no difference in GPIIIa platelet staining between wild-type and knockout mice. In tissue sections from control mice, there was no difference in the fluorescence pattern when wild-type mice as compared to the knockout mice. Increased platelet aggregation in blood vessels was observed at 6 hours following irradiation of wild-type mice. The percentage of blood vessels with platelet aggregation was abrogated in the P-selectin knockout mouse. Radiation-induced platelet aggregation was present in 10% of blood vessels as compared to 85% in wild type mice.

To determine whether x-ray-induced platelet aggregation is also attenuated in angiogenic blood vessels in P-selectin −/− mice, syngeneic tumors were induced in the hind lmibs of P-selectin +/+ mice and knockouts. GL261 gliomas were induced in P-selectin −/− and P-selectin +/+ C57BL6 mice. Untreated control tumors showed no difference in baseline staining for GPIIIa. Following x-irradiation with 10 Gy, tumors were sectioned and stained for GP-IIIa. Irradiated tumors in P-selectin +/+ mice showed platelet aggregation at 6 h. Tumors in P-selectin −/− mice, however, showed no increase in GP-IIIa staining in blood vessels at 1, 4, 6 or 24 hours after irradiation as compared to untreated controls.

GPIIIa staining showed that platelets extravasated from irradiated blood vessels into irradiated tissues. Red blood cells also extravasated into irradiated tissues. Platelets and RBC's within the lungs of irradiated P-selectin −/− mice were also studied. P-selectin −/− mice treated with 10 Gy thoracic irradiation developed tachypnea and respiratory distress within seven days. In contrast, P-selectin +/+ mice showed no evidence of respiratory distress following 16 Gy thoracic irradiation. Histologic sections of lungs from P-selectin −/− mice at seven days following irradiation show hemorrhage into the alveoli. In contrast, P-selectin +/+ mice show no extravasation of blood components into the irradiated lung.

EXAMPLE 3

X-Ray-Induced P-Selectin Localization to the Lumen of Tumor Blood Vessels

P-selectin is a cell adhesion molecule that is sequestered in Weibel-Palade storage reservoirs within the vascular endothelium and α granules in platelets. P-selectin is rapidly translocated to the vascular lumen after tissue injury to initiate the adhesion and activation of platelets and leukocytes. In this Example, the histologic pattern of P-selectin expression in irradiated tumor blood vessels was studied. P-selectin was localized within the endothelium of tumor vessels prior to irradiation. At one to six hours following irradiation, P-selectin was mobilized to the lumen of blood vessels.

To determine whether radiation-induced vascular lumen localization of P-selectin was tumor type-specific or species-specific, tumors in rats, C3H mice, C57BL6 mice and nude mice were studied. P-selectin localization to the vascular lumen was present in all tumors and all species studied. Irradiated intracranial gliomas showed P-selectin localization to the vascular lumen within one hour, whereas blood vessels in normal brain showed no P-selectin staining in the endothelium and no localization to the irradiated vascular lumen. Radiation-induced P-selectin localization to the vascular lumen increased in time-dependent manner, until 24 hours after irradiation.

P-selectin in platelets may account for the time dependent increase in staining within the vascular lumen after irradiation. Immunohistochemistry for platelet antigen GP-IIIa was utilized to differentiate between endothelial and platelet localization of P-selectin. It was found that GP-IIIa staining was not present at one hour after irradiation, but increased at 6 hours and 24 hours. P-selectin localization to the vascular lumen at 6 to 24 hours was, in part, associated with platelet aggregation. These findings indicate that radiation-induced P-selectin staining in the vascular lumen of neoplasms is associated with aggregation of platelets. Radiation-induced localization of P-selectin to the vascular lumen is specific to the microvasculature of malignant gliomas and is not present in the blood vessels of the irradiated normal brain.

METHODS

Maintenance of Tumor Cell Lines Tumors were induced by injection of tumor cells either subcutaneously or stereotactically into the rat brain. Rat C6 glioma cells were maintained in Ham's F10 medium with 15% horse serum, 2.5% fetal bovine serum, and 10 mM HEPES. Murine GL261 glioma cells were maintained in an F-12/DME 50% mixture and 7% fetal calf serum, and pen/strep. The human colon carcinoma cell line WIDR was maintained in MEMα, 1% NEAA and 10% fetal calf serum, and pen/strep.

Tumor induction in rodents Subconfluent tumor cells were trypsinized, washed, and injected subcutaneously into the hind limbs of mice. MCA4 tumors were excised, minced, and implanted by use of an 18-gauge needle subcutaneously into the hind limbs of C3H mice (Jackson Labs). Lewis lung carcinoma cells ($10^6$) were injected into the hind limbs of C57BL6 mice (Jackson Labs). Rat C6 cells were injected into Wistar rats (250–300 g) (Charles River, Wilmington, Mass.). Human colon carcinoma WIDR cells ($10^6$) were injected into nude mice (Jackson Labs). Tumors were grown to a volume of about 300 to about 500 $mm^3$ prior to treatment with radiation or cytokines.

Treatment of tumors with x-irradiation. Tumors were treated with 250 kV x-rays as described by Hallahan, D. E. et al., *Nature Medicine* 1:786 (1995), with 2, 4, or 10 Gy at a dose rate of 1 Gy per minute. At 1, 6, and 24 hours after irradiation, mice were sacrificed by intraperitoneal injection of xylazine and ketamine.

Immunohistochemical staining for expression of cell adhesion molecules. Formalin fixed tumors were embedded in paraffin blocks and sectioned (5 μm thick). Sections were placed unto SUPERFROST PLUS™ glass slides (Fisher Scientific). Tissue sections were baked at 60° C. for 1 hour, cleared in xylene, and hydrated through a descending alcohol series to distilled water. After brief washing in dd$H_2O$, endogenous activity was blocked by treatment of the sections with 3% hydrogen peroxide in methanol for 20 min. Two tissue sections from each case were then incubated overnight at 4° C. at a concentration of 2.5 μg/mL for anti-P-selectin monoclonal (Pharmigen, San Diego, Calif.) and anti-GP-IIIa (Pharmigen, San Diego, Calif.) monoclonal antibodies. One slide from each sample was treated in a similar fashion and incubated overnight in normal serum immunoglobulin (Ventana Medical Systems, Tucson, Ariz.). The immunohistochemical staining was performed on a Ventana GEN11™ system (Ventana Medical Systems). The Ventana GEN11™ uses an indirect strepavidin-biotin system conjugated with horseradish peroxidase for detecting the immunocomplex and diaminobenzidine as a substrate for localization. The Ventana GEN11™ uses a cartridge delivered avidin/biotin blocking kit to block endogenous biotin. The immunostained sections were counterstained with hematoxylin, dehydrated through an ascending alcohol series, cleared, and coverslipped. Stained sections were imaged under a 40x objective. All blood vessels throughout the entire section were observed, and 3 to 5 sections were analyzed for each tumor.

Brain tumor model. Intracranial gliomas were induced by stereotactic injection of rat C6 glioma cells into rat brains. Intracranial gliomas were allowed to grow for 14 days. C6 cells were maintained in Ham's F10 medium with 15% horse serum, 2.5% fetal bovine serum, and 10 mM HEPES. Growing cells were trypsinized and resuspended in PBS at $10^8$ cells/mL. Male Wistar rats (250–300 g) (Charles River, Wilmington, Mass.) were anaesthetized with a mixture of ketamine (90 mg/kg) and xylazine (10 mg/kg) and placed in a stereotactic frame (David Kopf Instruments, Tujunga, Calif.). The head was shaved and the skin incised, and a hole was drilled in the skull with a 1.8 mm trephine (Fine Science Tools Inc., Foster City, Calif.). Ten microliters of cell suspension were injected 4 mm beneath the surface of the skull with a 50 μl Hamilton syringe 2 mm from the midline and 2 mm anterior to the coronal suture. The skull was sealed with dental cement, the wound was stitched, and the animals were kept in separate cages for 2–3 days to prevent mutilation. Thirteen days after implantation, the animals were irradiated under anesthesia with 6 Gy (head only) in a $^{137}$Cs irradiator at 3.95 Gy /min. At 1, 6, 24, and 48 hours after irradiation, the animals were anesthetized again, and the brains were perfused with 10 mM sodium cacodylate, pH 7.0, 1.5% formaldehyde, 0.1% glutaraldehyde. The brains were further fixed in formaline, embedded in paraffin, and five micron sections processed as described.

RESULTS

X-ray induced localization of P-selectin to the lumen of tumor vascular endothelium. P-selectin is constitutively expressed in the endothelium of pulmonary blood vessels (Hallahan, D. E. et al., *Cancer Research* 56: 5150 (1996)) and is sequestered in Weibel Palade bodies and in storage reservoirs in the endothelium. To determine whether P-selectin is present in the vascular endothelium of tumors, immunohistochemistry for P-selectin was utilized. Blood vessels from mouse breast carcinoma tumors MCA4, mouse lung carcinoma (Lewis lung carcinoma), and human colon carcinoma xenografts (WIDR) were studied. P-selectin was present in the vascular endothelium of each of these tumors. This finding was independent of the implantation site (brain, flank, or hind limb), strain of mouse (C3H, C57BL6, or nude), and species (mouse versus rat).

To determine whether radiation induces P-selectin localization to the endothelium and/or the vascular lumen of tumor blood vessels, tumors were treated with x-rays and immunohistochemical analysis was performed using anti-P-selectin antibody. Radiation-induced P-selectin mobilization to the vascular lumen was observed in all tumors including MCA4 in C3H mice, Lewis lung carcinoma in C57BL6 mice, and WIDR tumor xenografts in nude mice. P-selectin localization to the vascular lumen occurred in all tumor types, independent of the location of the tumor, strain of mouse, and species of rodent models.

Radiation-induced P-selectin localization to the vascular lumen in C6 brain tumors. The vascular endothelium in the brain is distinct from the endothelium in peripheral tissues (Barkalow, F. J. et al., *Blood* 88:4585 (1996)). Moreover, Weibel-Palade bodies have been identified in blood vessels within gliomas (Miyagami, M. and Nakamura, S., *Noshuyo Byori* 13:107 (1996)). To determine whether malignant gliomas induced in the brain have a distinct P-selectin expression as compared to that in peripheral tumors, C6 gliomas were induced in the brains of Wistar rats. The entire brain was irradiated with 6 Gy and sectioned at 1 and 6 hours after treatment. The normal brain blood vessels showed no P-selectin in untreated controls or following irradiation. On the other hand, gliomas showed P-selectin staining in the endothelium of untreated tumors. At 1 hour after irradiation, P-selectin staining at the blood-tissue interface increased. At 6 hours after irradiation, P-selectin staining in the lumen of blood vessels increased intensely.

X-ray induced P-selectin localization to the vascular lumen is dose-dependent. The vascular response to ionizing radiation is both dose- and time-dependent (Hallahan, D. E. et al., *Biochemical & Biophysical Research Communications* 217:784 (1995); Hallahan, D. E. et al., *Cancer Research* 56:5150 (1996); Hallahan, D. E. & Virudachalam, S., *Proc. Natl. Acad. Sci. USA* 94:6432 (1997)). To determine the threshold and plateau doses for induction of P-selectin localization to the vascular lumen, 1, 2, 4, 10 and 20 Gy doses were utilized. No localization of P-selectin to the vascular lumen in tumors treated with 1 Gy was observed. Efficient localization of P-selectin to the vascular lumen occurred following irradiation with 2 Gy. There was no increase in P-selectin localization to the vascular lumen or degree of staining at 1 hour, when higher doses of x-rays were used. This finding suggested that P-selectin localization to the vascular lumen occurs at least about at 1 hour with a threshold dose of about 2 Gy.

P-selectin staining increases in a time-dependent manner. Time-dependent P-selectin staining in irradiated tumor blood vessels was studied to determine whether P-selectin expression increased over 24 hours. Tumors treated with 2 and 10 Gy were compared. It was found that there was no increase in expression over 24 hours in tumors treated with 2 Gy. On the other hand, 10 Gy did produce an increase in P-selectin staining that accumulated over 24 hours. P-selectin staining was present at a low baseline level at 1 hour, and increased at 6 and 24 hours.

Platelet staining with anti-GP-IIIa. As noted above, GP-IIIa is a platelet antigen that is not found in the vascular endothelium. Anti-GP-IIIa antibodies were utilized to determine whether the time-dependent increase in P-selectin staining is due to platelet aggregation. Lewis lung carcinoma tumors in C57BL6 mice were irradiated and stained with anti-GP-IIIa antibody. Little GP-IIIa staining was found in blood vessels at 1 hour following irradiation. However, GP-IIIa staining increased at 6 and 24 hour following irradiation. These findings indicate that the increased P-selectin staining within the vascular lumen of irradiated tumors was due to platelet aggregation.

EXAMPLE 4

Delivery of Platelet Vehicles to Irradiated Tissue in an Animal Subject

In accordance with the present invention, a non-invasive method of imaging platelet aggregation using indium-111 ($^{111}$In)-labeled platelet scan was performed in an animal model (mice) and was successful. Mice were exposed to lethal doses of 10.5 Gy whole body radiation. Renal uptake was shown within 2 hours of irradiation. For 4 subsequent days, the uptake of $^{111}$In platelets was significantly greater than in non-irradiated controls. This difference was amplified if the platelets were injected 3 days after irradiation and remained constant for the following 4 days.

EXAMPLE 5

Delivery of Platelet Vehicles to Irradiated Tissue in a Human Subject

Indium-111 ($^{111}$In)-labeled platelet scintigraphy has been extensively used in the study of thrombosis and platelet kinetics in human subjects. There are two ligands that are widely used and these are oxine and tropolone. Both techniques preserve platelet function. In normal subjects, almost all of the radioisotope is bound to platelets. There is a significant reduction in radiolabeling efficiency and decreased percentage of $^{111}$In bound to platelets in vivo for patients with platelet counts<150,000/mL (Giannessi, D. et al., *Nucl. Med. Biol.* 22(3):399–403 (1996)).

As the two methods of labeling are quite comparable and oxine is commercially available and FDA approved for the study of platelets, $^{111}$In-oxine labeled platelets are utilized in this Example. The distribution of $^{111}$In-labeled platelets has been studied in normal volunteers, and $^{111}$In platelet imaging is a diagnostic protocol already in place at many medical facilities, including, for example, Vanderbilt Medical Center, Nashville, Tenn. Radioactivity in the lungs, heart, spleen, kidneys and testes have been determined for up to 75 hours after injection. After the first four hours, the activity in each of these organs, except liver and kidney, decreases at roughly the physical decay rate. The curves for the liver and kidney are flat and indicate continued accumulation of the radiotracer. The calculated mean radiation dose per unit administered activity is 0.6±0.7 rad/mCi for the total body and 34±6 rad/mCi for the spleen (Robertson, J. S. et al., *Radiology* 140(1):169–176 (1981)). The safety of $^{111}$In platelet scans in patients, including those with malignancies, has been well established (Oriuchi, N. et al., *European Journal of Nuclear Medicine* 25(3):247–252 (1998)).

Although planar images can give excellent information about the uptake especially in lesions of the extremities, or head and neck region, the presence of background uptake in overlying and underlying normal tissues such as the liver, spleen, and heart make the interpretation of intrathoracic and intraabdominal lesions more difficult. To get a better definition (i.e. improved contrast ratio) of three-dimensional (3D) uptake, SPECT functional imaging, in conjunction with CT or MRI images, is utilized. SPECT imaging with $^{111}$In labeled autologous platelets has been shown to provide increased image contrast and improved quantification over planar images (Suga, K. et al., *Clin Nucl Med* 8:595–601 (1996); Bacq, Z. M. et al., *Journal of Physiology* 273:42P–43P (1977)).

Patients are stratified between intracranial and peripheral tumors at the time of registration. In patients, 42 mL of whole blood is collected, and platelets are separated and labeled with $^{111}$In oxine (Thakur ML 981) as described below. Patients are injected with $^{111}$In oxine platelets preferably as soon as possible. (Anticipate approximately two hours following obtaining blood sample)

Patients are imaged 2–4 hours following injection of labeled platelets. Static images are obtained using a gamma camera fitted with a medium energy collimator peaked for 173–247 keV and 20% energy window. This is the Pre-RT scan to determine the baseline uptake in untreated tumors. Patients then begin radiation therapy. The dose per fraction, as well as the total dose, are determined by the treating radiation oncologist. 24–72 hours after injection of $^{111}$In oxine platelet, the patient is re-imaged. This is the Post-RT scan.

Radiation Therapy

Modality: External beam photon irradiation

Energy: 4–18 MV photon beams. Appropriate blocks, wedges, and bolus to deliver adequate dose to the planned target volume. Minimum source-axis distance of 80 cm.

Treatment Volume: All patients will receive local-regional irradiation. Fields are designed to encompass sites of disease requiring palliation or primary treatment. All fields must be treated each day.

Study, site, treatment intent and normal tissue considerations determine dose. Patients are stratified to either intracranial or peripheral tumors and Inverse dose escalation is conducted in these two groups independently. When stereotactic radiotherapy is used, the dose is prescribed to the tumor periphery.

Inverse ionizing radiation dose escalation of cohorts of 3*:

800–1200 cGy/1 fraction 2000 cGy/5 fractions 3000 cGy/10 fractions 3500 cGy/15 fractions 6000 cGy/30 fractions

*Note: A failure to detect $^{111}$In is detected in tumors of three patients treated with 1000 cGy indicates that the alternative schema set forth herein below are to be followed. The observation of $^{111}$In uptake in tumors in 2 of 3 patients provides for the expansion of the cohort to a total of 6 patients. The observation of $^{111}$In uptake in tumors in 3 of 6 or 1 of 3 patients indicates that the dose is below threshold and the alternative schema set forth herein below are to be followed.

Dose Modifications And Management of Toxicity Dose modifications and management of toxicity secondary to radiation are left to the judgment of the treating radiation oncologist. No side effects are expected from the $^{111}$In oxine platelet scan.

Evaluation. Scans are evaluated degree of uptake on post-RT scans is compared to pre-RT scans on the same patient. The pharmacokinetics and pharmacodynamics of $^{111}$In uptake in tumors are determined by comparing scans obtained pre-RT to that obtained post-RT. If $^{111}$In is not visualized at a particular dose level, SPECT scanning is performed.

Alternative Schema. Visualization of $^{111}$In in fewer than 2 of 3 or 4 of 6 patients suggests that platelets might have been inactivated by $^{111}$In labeling. An alternative embodiment considers $^{99m}$Tc labeling and pretreatment of platelets with DDAVP (depoprovera). A greater number of fractions may be required to achieve platelet aggregation. Platelets may be given after the second and third fraction of irradiation. The pharmacokinetics may be too brief for gamma camera detection, and thus, scans should be performed at 1 to 6 hours after irradiation.

Platelets might be sequestered in spleen, etc. If so, the schedule of administration is changed to radiation followed immediately by radiolabeled-platelet administration.

Statistical Considerations. The observation of $^{111}$In uptake in tumors in 2 of 3 patients provides for the expansion of the cohort to a total of 6 patients. The observation of $^{111}$In uptake in tumors in 3 of 6 or 1 of 3 patients indicates that the dose is below threshold and the alternative schema described above are followed. In either case, quantification of gamma-ray detection is measured. Pharmacokinetics of $^{111}$In uptake is determined by comparing scans from day 1 to scans from day 2 at each dose level.

Drug Formulation, Availability, And Preparation. As would be appreciated by one of ordinary skill in the art, preparation, handling, and safe disposal of radioactive agents are performed in a self-contained, protective environment. Unused portions of radiolabeled platelets are discarded in appropriate labeled containers.

Drug Information.

Drug name: Indium-111 ($^{111}$In)

Availability: Amersham

Storage and Stability: Platelets are preferably administered immediately after labeling with $^{111}$In Toxicity: No anticipated toxicities.

Platelet Labeling.

Preparation. 42 mL of whole blood collected in 8 mL of modified squibb ACD solution. Transfer to two 50 mL sterile propylpropylene tubes without the plunger or needle and very gently resuspend the blood with a pipette. Centrifuge 200 g maximum (900 RPM RC-3B) for 10 minutes. Separate platelet rich plasma (PRP), leaving 0.5–0.6 cm on the RBC layer and transfer to 12 mL sterile sarstedt conical tube. Centrifuge 1650 g maxim (2600 RPM) for 10 minutes. Transfer the platelet poor plasma (PPP) by pouring into sterile 12 mL tube. Suspend the platelet pellet in 4–5 mL of ACO saline and centrifuge for 5 minutes at 2600 RPM. Remove the supernatant and add 550–600 μCi $^{111}$In oxine with a sterile pipette to the platelet pellet. Mix with sterile pipette (5 gentle suctions up and down, do not introduce air bubbles. Incubate at room temperature for 20 minutes.

Centrifuge the $^{111}$In platelet tube at 1650 g maximum (2600 RPM) for 10 minutes. Save the supernatant. Determine supernatant activity using a dose calibrator. Resuspend In-platelets in 5 mL ACD/saline solution. Centrifuge 1650 g maximum (2600 RPM) for 8 minutes. Remove the supernatant and determine radioactivity of supernatant. Resuspend in 5 mL of ACD/saline. Centrifuge at 100 g maximum (500 RPM) for 5 minutes. Remove the supernatant and resuspend the $^{111}$In-platelets in 5 mL of PPP. Withdraw 5 mL of $^{111}$In platelets in a sterile syringe using a 19 gauge needle. Place an aliquot in a tube to send for CBC. Measure and document radioactivity.

Administration. The patient is injected with a 19 gauge needle and residual activity is measured. Labeling efficiency is determined and number of platelets used for labeling is calculated from CBC.

EXAMPLE 6

X-Ray-Guided Drug Delivery by Radiation-Induced Aggregation of Electroporated Platelets This Example discloses the use of electroporation to prepare loaded platelets and contemplates reduced binding within the reticular endothelial system (RES) by platelets so prepared. In this Example, fluorochromes (Cy3, FITC) and gamma emitting radionuclides are loaded into platelets by use of electroporation. Additionally, small molecular weight compounds, which are inert in untreated tissues but demonstrate cytotoxicity in cells treated with ionizing radiation as disclosed herein, are also electroporated into platelets. Fluorescent markers (Cy3, FITC) are electroporated into platelets so that they can be identified by fluorescent microscopy.

Platelets are also loaded using the open channel system (OCS), receptor-mediated endocytosis using retention of liposomes, or reconstituted Sendai virus envelopes (RSVE). These techniques have been used to load chemotherapeutic agents such as adrimycin, cis-platinum and radioisotopes. Platelets are loaded by liposomes comprising chole steryl hexa decyesyl ether or chole steryl oleate. The liposome mediated platelet encapsulation is compared to electroporation using techniques described by Crawford, N., *Semin. Intervent. Cardiol.* 1:91–102 (1996). Platelets are also loaded with radiation sensitizing drugs in a similar manner for similar comparison. The loaded platelet delivery vehicles are then administered to a vertebrate subject and the target tissue is exposed to ionizing radiation via intersecting planes of irradiation in accordance with the methods of the present invention, including those set forth the foregoing Examples.

In separate experiments, platelets are loaded with $^{111}$In for studies of biodistribution and pharmacokinetics using gamma camera imaging and phospho imager plates to determine whole body biodistribution. Validation of Image Processing is performed by use of autoradiography and immunofluorescence of platelet antigen GP II/IIIa as described by Hallahan et al., *Cancer Research*, 58:5126–5220 (1998).

Improved biodistribution and pharmacokinetics are contemplated by optimizing the time interval, schedule and route of administration. Radiation sensitizing compounds such as the DNA PK inhibitor, R106 (ICOS, Inc., Borthwall, Wash.), or tyrosine kinase inhibitor, Su5416 (Sugen, Inc., and Fong et al., *Cancer Research* 59:99–106 (1999) and SU6668 (Sugen Inc., Redwood City, Calif.) are delivered, resulting in enhancement of subsequently delivered, intersecting planes of radiotherapy.

EXAMPLE 7

X-Ray-Guided Drug Delivery Using GP-IIb/IIIa Binding Delivery Vehicles

This Example discloses the delivery of specific activity of therapeutic radionuclides to tumors by x-ray-guided delivery of microspheres and biapcitide. The objective of this Example is to improve the specificity of drug delivery to irradiated tissues by reducing nonspecific binding within the RES.

Fibrinogen is covalently bound to the surface of cross-linked human albumin in accordance with techniques disclosed in U.S. Pat. Nos. 5,069,936; 5,308,620; 5,725,804; 5,716,643; and 5,616,311, herein incorporated by reference. Briefly, fibrinogen-coated microspheres (available form Hemosphere, Inc., Irvine, Calif. as thrombspheres) ranging from 100 nm to 1 μm were produced from albumin microaggregates. The microspheres were re-suspended using 10 mL of sterile normal saline (0.9% NaCl) and 0.5 mL of the reconstituted microspheres was added to a 1.5 mL conical polypropylene tube previously coated with IODOGEN™ (Pierce Chemical Company). 11.3 mCi (0.42 GBq) of 1–131 in approximately 11 μL was added to the microspheres and allowed to incubate at room temperature for 30 minutes.

Following incubation, the microspheres were transferred to a 15 mL sterile centrifuge tube, diluted to 10 mL with normal saline and centrifuged at 1,500×g for 7 minutes. The supernatant was removed and discarded. The microspheres were washed one additional time with 10 mL of normal saline. Following the final wash, the microspheres were suspended in 2 mL of normal saline for injection. Final yield was 4.8 mCi (0.18 GBq) of radioiodinated microspheres in 2 mL saline. Radiochemical yield was 42.4%.

C57BL6 mice bearing Lewis Lung Carcinoma hind limb tumors were treated in three manners: 1) control mice received $^{131}$I-microspheres, but no irradiation, 2) 10 Gy prior to $^{131}$I-microspheres, 3) 10 Gy immediately after $^{131}$I-microsphere injection. Whole body gamma camera images were obtained by pinhole planer imaging. Untreated tumors showed no binding of microspheres within tumors, but there was uptake in liver and spleen. Tumors treated with 10 Gy prior to microsphere administration showed $^{131}$I uptake in tumors within 1 hour and persistent uptake in tumors beyond 24 hours. Gamma detection was also observed in the liver and spleen. Tumors treated with 10 Gy immediately after radiolabeled microsphere injection showed 10-fold greater uptake in tumors as compared to tumors treated with 10 Gy before injection. There was minimal uptake in the liver and spleen in these animals.

In separate experiments, apcitide is labeled with $^{99}$Tc in accordance with a protocol provided by Diatide Inc, a commercial source. Apcitide is a fibrinogen analogue peptide that binds to GPIIb/IIIa on activated platelets, as described by Taillefer, J., *Nucl. Med.* 38:5 (1997) and by VandeSreek, P., *Eur. J. Nucl. Med.* 25:8 (1998). Radiolabeled apcitide is then injected by tail vein into mice bearing hind limb tumors. Mouse tumors are treated with radiation as described herein above. An optimal schedule of administration is determined.

The platelet priming agent, DDAVP (depo-provera), is contemplated to improve radiation induced platelet aggregation within tumors and thereby lower the radiation threshold dose for GP-IIb/IIIa binding. The enhancement of platelet aggregation with DDAVP is also contemplated to enhance binding of radiolabeled peptides and microspheres. Thus, in additional experiments, DDAVP is administered in conjunction with the radiolabeled peptides and microspheres and with the exposure of the target tissue to radiation. Validation of Image Processing is performed by use of autoradiography and immunofluorescence of platelets GP IIb/IIIa.

X-ray-guided drug delivery can thus be achieved by use of fibrinogen-coated microspheres and by peptides which preferentially bind activated platelets. Improved biodistribution and pharmacokinetics are observed with microspheres in that the microspheres bind more preferentially to activated platelets as compared to RES, and all activated platelets represent targets for drug delivery.

EXAMPLE 8

X-Ray-Guided Drug Delivery by Use of Anti-Platelet Antibody Delivery Vehicles Following platelet activation, several antigens are expressed on the surface of platelets. Indeed, it has been observed that irradiation of animal tumors increases the expression of platelet antigens such as P-selectin and GP-IIb/IIIa. As disclosed herein above, antibodies can be conjugated to radionuclides, cytotoxic agents, gene therapy vectors, liposomes and other active agents. In this Example, the administration of radioimmunoconjugate delivery vehicles against platelet antigens following irradiation of tumors is disclosed.

Anti-GP-IIb/IIIa antibodies (R&D Systems) are labeled with $^{131}$I using IODOGEN™ (Pierce Chemical Company). Labeled antibody is separated from free iodine by use of column chromatography. Radioimmunoconjugates are injected into mice by tail vein. Hind limb tumors are implanted and treated as described herein above. The optimal time of administration of radioimmunoconjugates is determined.

In separate experiments, procoagulants such as DDAVP are also administered to enhance radioimmunoconjugate binding to activated platelets in irradiated tumors. Mouse subjects are imaged by gamma camera as described herein above. Phosphoimager plates and histologic sections with immunohistochemistry as described herein above are used to validate image processing. In the event that certain radioimmunoconjugates do not achieve specific activity within tumors that is sufficient to image or treat tumors, multiple radionuclides are incorporated into the antibody delivery vehicles.

EXAMPLE 9

X-Ray-Guided Drug Delivery Targeted to Radiation-Induced Antigens in Blood Vessels Radiation-induced targets for drug delivery systems will be most useful if they are not tumor-specific. The vascular endothelium is an essential component to nearly all neoplasms. As disclosed herein above, radiation response is similar across a wide range of tumor types. In particular, P-selectin exocytosis, von Willebrand Factor release and platelet aggregation are observed within all tumor blood vessels following irradiation. In this Example, antibody delivery vehicles for x-ray-guided drug delivery to the vascular endothelium of tumors is disclosed. Antibody delivery vehicles adhere to antigens released into the lumen and are thus obstructed from circulating beyond the confines of the tumor. In view of the targeting of vascular endothelium, this Example is contemplated to be illustrative of the methods of treating angiogenesis in accordance with the present invention disclosed herein above.

Hind limb tumors are implanted into mice and treated with radiation as described by Hallahan, D. E. et al., *Cancer Research*, 58:5126–5220 (1998). Radioimmunoconjugate delivery vehicles are prepared using anti-E-selectin and anti-P-selectin antibodies (R&D Systems), IODOGEN™ (Pierce Chemical Company) and $^{131}$I. Radiolabeled antibodies are separated from free $^{131}$I by use of column chromatography. The delivery vehicles are injected via tail vein into mice with hind limb tumors following treatment with irradiation. Mice are imaged with gamma camera imaging as described herein above. Image processing is validated by use of phospho imager plates, immunofluorescence and immuno-histochemistry as described herein above.

One potential limitation of this embodiment of the present invention is that anti-E-selectin antibody binding occurs in untreated normal tissues such as the lung. The importance of validation of the tumor specificity for radioimmunoconjugate delivery vehicles is that the ideal radiation-induced antigens have substantially no constitutive expression in any tissue, but prolonged expression in tumor blood vessels. Thus, pharmacokinetics and biodistribution of the anti-E-selectin and anti-P-selectin antibody delivery vehicles are also determined.

REFERENCES

The references listed below as well as all references cited in the specification are incorporated herein by reference to the extent that they supplement, explain, provide a background for or teach methodology, techniques and/or compositions employed herein.

Ausprunk et al., *Am. J. Pathol.*, 79:597–618 (1975).
Ausubel et al., *Current Protocols in Molecular Biology*, Greene Publishing Associates and Wiley Interscience, N.Y. (1989).
Bacq, Z. M. et al., *Journal of Physiology* 273:42P–43P (1977).
Barkalow, F. J. et al., *Blood* 88:4585 (1996).
Bittner et al., *Methods in Enzymol.* 153:516–544 (1987).
Boukerche, H., *British Journal of Haematology* 92:442–51 (1996).
Brooks, P. C., *Cancer Metastasis Rev* 15:187–194 (1996).
Colberre-Garapin et al., *J. Mol. Biol.* 150:1 (1981).
Crawford, N., *Semin. Intervent. Cardiol.* 1:91–102 (1996).
DeVita, V. T. Jr., in *Harrison's Principles of Internal Medicine*, p.68, McGraw-Hill Book Co., N.Y. (1983).
Dillman et al,. *Antibody Immunocon. Radiopharm* 1:65–77 (1988). European Patent No. 44167
Eyden, B. P., *Journal of Submicroscopic Cytology & Pathology* 25:145–8 (1993).
Fletcher, G. H., *Textbook of Radiotherapy*. Philadelphia, Lea and Febiger (1975).
Flickinger & Trost, *Eu. J. Cancer* 12(2):159–60 (1976).
Folkman, J., *N Engl J Med* 28;333(26):1757–1763 (1995).
Gabe, D. *Radiotherapy & Oncology* 30:199–205 (1994).
Ghose et al., *CRC Critical Reviews in Therapeutic Drug Carrier Systems* 3:262–359 (1987).
Ghose et al., *Meth. Enzymology* 93:280–333 (1983).
Giannessi, D. et al., *Nucl. Med. Biol.* 22(3):399–403 (1996).
Hailing et al., *Nucl Acids Res* 13:8019–8033 (1985).
Hainfeld, *J. Proc. Natl. Acad. Sci. USA* 89:11064–11068 (1992)

Hallahan et al., *Cancer Research,* 58:5126–5220 (1998).
Hallahan, D. E. et al., *Nature Medicine* 1:786–791 (1995).
Hallahan, D. E. and Virudachalam, S., *Proc. Natl. Acad. Sci. USA* 94:6432–7 (1997).
Hallahan, D. E. et al., *Cancer Research* 56:5150–5155 (1996).
Hallahan, D. E. et al., *Biochemical & Biophysical Research Communications* 217:784–795 (1995).
Hallahan, D. E. and Virudachalam, S., *Cancer Research* 57:2096–2099 (1997).
Inouye et al., *Nucleic Acids Res.* 13:3101–3109 (1995).
Kimura et al., *Immunogenetics* 11:373–381 (1980).
Knowles and Thorpe, *Anal. Biochem.* 120:440–443 (1987).
Kohler and Milstein, *Nature* 256:495–497 (1975).
Kwok, C. S. et al. (1985) *Med. Phys.* 12:405.
Lamb et al., *Eur Jrnl Biochem* 148:265–270 (1985).
Logan et al., *Proc. Natl. Acad. Sci. USA* 81:3655–3659 (1984).
Lord et al., In *Genetically Engineered Active Agents* (Ed. A. Frank, M. Dekker Publ., p. 183) (1992).
Lowy et al., *Cell* 22:817 (1980).
Markoe, A. M., *Radiation Oncologic Emergencies, in Principles and Practice of Radiation Oncology* 1267–1270 (1987).
Mayadas et al. *Cell* 74:541–54 (1993).
Miyagami, M. and Nakamura, S., *Noshuyo Byori* 13:107 (1996).
Mulligan et al., *Proc. Natl. Acad. Sci. USA* 78:2072 (1981).
O'Hare et al., *FEBS Lett* 210:731 (1987).
O'Hare et al., *Proc. Natl. Acad. Sci. USA* 78:1527 (1981).
Ogata et al., *J. Biol. Chem.* 256:20678–20685 (1990).
Oriuchi, N. et al., *European Journal of Nuclear Medicine* 25(3):247–252 (1998).
Ossonski et al., *Cancer Res.,* 40:2300–2309 (1980).
Pietersz et al., *Antibody Immunocon. Radiopharm.* 1:79–103 (1988).
Remington's *Pharmaceutical Sciences,* 16th Ed. Mack Publishing Company (1980).
Robertson, J. S. et al., *Radiology* 140(1):169–176 (1981).
Ruther et al., *EMBO J* 2:1791 (1983).
Sambrook et al., *Molecular Cloning, A Laboratory Manual,* Cold Spring Harbor Laboratory, N.Y. (1989).
Santerre et al., *Gene* 30:147 (1984).
Sinha, S. and Wagner, D. D., *European Journal of Cell Biology* 43:377–83 (1987).
Smith et al, *J. Virol.* 46:584 (1985).
Spitler L. E., et al. *Cancer Res.* 47:1717 (1987).
Subramaniam et al., *Blood* 87:1238–42 (1996).
Suga, K. et al., *Clin Nucl Med* 8:595–601 (1996).
Szybalska et al., *Proc. Natl. Acad. Sci. USA* 48:2026 (1962).
Taillefer, J., *Nucl. Med.* 38:5 (1997).
Thorpe et al., *Cancer Res.* 47:5924–5931 (1987).
U.S. Pat. No. 4,215,051
U.S. Pat. No. 4,340,535
U.S. Pat. No. 4,472,509
U.S. Pat. No. 5,069,936
U.S. Pat. No. 5,292,524
U.S. Pat. No. 5,308,620
U.S. Pat. No. 5,328,840
U.S. Pat. No. 5,612,318
U.S. Pat. No. 5,616,311
U.S. Pat. No. 5,641,755
U.S. Pat. No. 5,716,643
U.S. Pat. No. 5,725,804
U.S. Pat. No. 5,753,230
U.S. Pat. No. 5,770,581
U.S. Pat. No. 5,776,427
U.S. Pat. No. 5,817,636
Vaickus et al., *Cancer Invest.* 9:195–209 (1991).
VandeSreek, P., *Eur. J. Nucl. Med.* 25:8 (1998).
Van Heeke et al., 264:5503–5509 (1989).
Vogel & Muller-Eberhard, *Anal. Biochem* 118(2):262–268 (1981).
Wessels, B. W. and Rogus, R. D. *Med. Phys.* 11:638 (1984).
Wigler et al., *Cell* 11:223 (1977).
Wigler et al., *Proc. Natl. Acad. Sci. USA* 77:3567 (1980).
Wu et al., *British Journal of Cancer* 68:883–9 (1994).
Zola, *Monoclonal Antibodies: a Manual of Techniques,* CRC Press, Inc. (1987).

It will be understood that various details of the invention may be changed without departing from the scope of the invention. Furthermore, the foregoing description is for the purpose of illustration only, and not for the purpose of limitation—the invention being defined by the claims.

---

---

What is claimed is:

1. A method of targeting a tissue in a vertebrate subject for delivery of an active agent, the method comprising:
   exposing the tissue to ionizing radiation before, after, during, or combinations thereof, administration of a platelet comprising the active agent to the vertebrate subject, and
   wherein the tissue is targeted for the delivery of the platelet by the exposing of the tissue to ionizing radiation.

2. The method of claim 1, further comprising administering the platelet comprising the active agent about one hour prior to exposing the tissue to ionizing radiation.

3. The method of claim 1, further comprising administering the platelet comprising the active agent about ten minutes after exposing the tissue to ionizing radiation.

4. The method of claim 1, further comprising administering the platelet comprising the active agent both at about one hour prior to and at about ten minutes after exposing the tissue to ionizing radiation.

5. The method of claim 1, wherein the platelet comprising the active agent is administered after exposing the tissue to ionizing radiation.

6. The method of claim 1, wherein the tissue is exposed to an ionizing radiation dose ranging from about 0.1 to about 150 Gy.

7. The method of claim 6, wherein the tissue is exposed to an ionizing radiation dose ranging from about 2 to about 100 Gy.

8. The method of claim 7, wherein the tissue is exposed to an ionizing radiation dose ranging from about 4 to about 50 Gy.

9. The method of claim 8, wherein the target tissue is exposed to an ionizing radiation dose ranging from about 10 to about 20 Gy.

10. A method of delivering an active agent to a target tissue in a vertebrate subject, the method comprising the steps of:
(a) exposing the target tissue to ionizing radiation to target the tissue for a platelet; and
(b) administering a platelet to the vertebrate subject before, after, during, or combinations thereof, exposing the target tissue to the ionizing radiation, the platelet comprising the active agent, whereby the platelet localizes in the target tissue to thereby deliver the agent to the target tissue.

11. The method of claim 10, wherein the platelet comprising the active agent is administered about one hour prior to exposing the target tissue to ionizing radiation.

12. The method of claim 10, wherein the platelet comprising the active agent is administered about ten minutes after exposing the target tissue to ionizing radiation.

13. The method of claim 10, wherein the platelet comprising the active agent is administered both at about one hour prior to and at about ten minutes after exposing the target tissue to ionizing radiation.

14. The method of claim 10, wherein the method further comprises the initial step of loading the platelet with an active agent via electroporation.

15. The method of claim 10, wherein the platelet comprising the active agent is administered after exposing the tissue to ionizing radiation.

16. The method of claim 10, wherein the target tissue is exposed to an ionizing radiation dose ranging from about 0.1 to about 150 Gy.

17. The method of claim 16, wherein the target tissue is exposed to an ionizing radiation dose ranging from about 2 to about 100 Gy.

18. The method of claim 17, wherein the target tissue is exposed to an ionizing radiation dose ranging from about 4 to about 50 Gy.

19. The method of claim 18, wherein the target tissue is exposed to an ionizing radiation dose ranging from about 10 to about 20 Gy.

20. The method of claim 10, wherein the active agent comprises an imaging agent.

21. The method of claim 20, wherein the imaging agent is selected from the group consisting of paramagnetic, radioactive and fluorogenic ions.

22. The method of claim 21, wherein the radioactive imaging agent is selected from the group consisting of gamma-emitters, positron-emitters and x-ray-emitters.

23. The method of claim 21, wherein the radioactive imaging agent is selected from the group consisting of $^{43}K$, $^{52}Fe$, $^{57}Co$, $^{67}Cu$, $^{67}Ga$, $^{68}Ga$, $^{77}Br$, $^{81}Rb$, $^{81M}Kr$, $^{87M}Sr$, $^{99M}Tc$, $^{111}In$, $^{113}In$, $^{123}I$, $^{125}I$, $^{127}Cs$, $^{129}Cs$, $^{131}I$, $^{132}I$, $^{197}Hg$, $^{203}Pb$ and $^{206}Bi$.

24. The method of claim 21, wherein the radioactive imaging agent is present in the platelet in an amount ranging from about 0.1 to about 100 millicuries.

25. The method of claim 24, wherein the radioactive imaging agent is present in the platelet in an amount ranging from about 1 to about 10 millicuries.

26. The method of claim 25, wherein the radioactive imaging agent is present in the platelet in an amount ranging from about 2 to about 5 millicuries.

27. The method of claim 26, wherein the radioactive imaging agent is present in the platelet in an amount ranging from about 1 to about 5 millicuries.

28. The method of claim 9, wherein the active agent comprises a therapeutic agent.

29. The method of claim 28, wherein the therapeutic agent is selected from the group consisting of a chemotherapeutic agent, a toxin, a radiotherapeutic agent, a radiosensitizing agent and combinations thereof.

30. The method of claim 29, wherein the chemotherapeutic agent is selected from the group consisting of an anti-tumor drug, a cytokine, an anti-metabolite, an alkylating agent, a hormone, methotrexate, doxorubicin, daunorubicin, cytosine arabinoside, etoposide, 5-4 fluorouracil, melphalan, chlorambucil, a nitrogen mustard, cyclophosphamide, cis-platinum, vindesine, vinca alkaloids, mitomycin, bleomycin, purothionin, macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin, and combinations thereof.

31. The method of claim 29, wherein the toxin is selected from the group consisting of Russell's Viper Venom, activated Factor IX, activated Factor X, thrombin, phospholipase C, cobra venom factor, ricin, ricin A chain, Pseudomonas exotoxin, diphtheria toxin, bovine pancreatic ribonuclease, pokeweed antiviral protein, abrin, abrin A chain, gelonin, saporin, modeccin, viscumin, volkensin and combinations thereof.

32. The method of claim 29, wherein the radiotherapeutic agent is selected from the $^{47}Sc$, $^{67}Cu$, $^{90}Y$, $^{109}Pd$, $^{123}I$, $^{125}I$, $^{131}I$, $^{186}Re$, $^{188}Re$, $^{199}Au$, $^{211}At$, $^{212}Pb$, $^{212}Bi$, $^{32}P$, $^{33}P$, $^{7}Ge$, $^{77}As$, $^{103}Pb$, $^{105}Rh$, $^{111}Ag$, $^{119}Sb$, $^{121}Sn$, $^{131}Cs$, $^{143}Pr$, $^{161}Tb$, $^{177}Lu$, $^{191}Os$, $^{193M}Pt$, and $^{197}Hg$.

33. The method of claim 29, wherein the radiosensitizing agent is selected from the group consisting of an anti-angiogenic agent; a DNA protein kinase inhibitor; a tyrosine kinase inhibitor; a DNA repair enzyme inhibitor; nitroimidazole; metronidazole; misonidazole; a genetic construct comprising an enhancer-promoter region which is responsive to radiation, and at least one structural gene whose expression is controlled by the enhancer-promoter; boron-neutron capture reagents; and combinations thereof.

34. The method of claim 33, wherein the genetic construct further comprises a viral vector.

35. The method of claim 29, wherein the therapeutic agent is a chemotherapeutic agent, and the chemotherapeutic agent is administered in an amount ranging from about 10 to about 1000 mg.

36. The method of claim 35, wherein the chemotherapeutic agent is administered in an amount ranging from about 50 to about 500 mg.

37. The method of claim 36, wherein the chemotherapeutic agent is administered in an amount ranging from about 100 to about 250 mg.

38. The method of claim 29, wherein the therapeutic agent is a toxin, and the toxin is administered in an amount ranging from about 1 to about 500 µg.

39. The method of claim 38, wherein the toxin is administered in an amount ranging from about 10 to about 100 µg.

40. The method of claim 39, wherein the toxin is administered in an amount ranging from about 20 to 50 µg.

41. The method of claim 40, wherein the neoplasm is exposed to an ionizing radiation dose ranging from about 10 to about 20 Gy.

42. The method of claim 29, wherein the therapeutic agent is a radiotherapeutic agent, and the radiotherapeutic agent is administered in an amount ranging from about 0.5 to about 100 mg.

43. The method of claim 42, wherein the radiotherapeutic agent is administered in an amount ranging from about 1 to about 50 mg.

44. The method of claim 43, wherein the radiotherapeutic agent is administered in an amount ranging from about 5 to about 10 mg.

45. The method of claim 10, wherein the target tissue comprises a neoplasm.

46. The method of claim 45, wherein the neoplasm is selected from the group consisting of benign intracranial melanomas, arteriovenous malformation, angioma, macular degeneration, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, solid tumors, solid tumor metastases, angiofibromas, retrolental fibroplasia, hemangiomas, Karposi's sarcoma and combinations thereof.

47. The method of claim 10, wherein the vertebrate subject is a mammal.

48. The method of claim 47, wherein the mammal is a human.

49. A method of treating a neoplasm in a vertebrate subject, the method comprising the steps of:
(a) exposing the neoplasm to ionizing radiation to target the neoplasm for a platelet; and
(b) administering a platelet to the vertebrate subject before, after, during, or combinations thereof, exposing the neoplasm to the ionizing radiation, the platelet comprising a therapeutic agent, whereby the platelet delivers the therapeutic agent to the neoplasm to thereby treat the neoplasm.

50. The method of claim 49, wherein the neoplasm is selected from the group consisting of benign intracranial melanomas, arteriovenous malformation, angioma, macular degeneration, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, solid tumors, solid tumor metastases, angiofibromas, retrolental fibroplasia, hemangiomas, Karposi's sarcoma and combinations thereof.

51. The method of claim 49, wherein the platelet comprising the therapeutic agent is administered about one hour prior to exposing the target tissue to ionizing radiation.

52. The method of claim 49, wherein the platelet comprising the therapeutic agent is administered about ten minutes after exposing the target tissue to ionizing radiation.

53. The method of claim 49, wherein the platelet comprising the therapeutic agent is administered both at about one hour prior to and at about ten minutes after exposing the target tissue to ionizing radiation.

54. The method of claim 49, wherein the method further comprises the initial step of loading the platelet with an active agent via electroporation.

55. The method of claim 49, wherein the platelet comprising the therapeutic agent is administered after exposing the neoplasm to ionizing radiation.

56. The method of claim 49, wherein the neoplasm is exposed to an ionizing radiation dose ranging from about 0.1 to about 150 Gy.

57. The method of claim 56, wherein the neoplasm is exposed to an ionizing radiation dose ranging from about 2 to about 100 Gy.

58. The method of claim 57, wherein the neoplasm is exposed to an ionizing radiation dose ranging from about 4 to about 50 Gy.

59. The method of claim 49, wherein the therapeutic agent is selected from the group consisting of a chemotherapeutic agent, a toxin, a radiotherapeutic agent, a radiosensitizing agent and combinations thereof.

60. The method of claim 59, wherein the chemotherapeutic agent is selected from the group consisting of an anti-tumor drug, a cytokine, an anti-metabolite, an alkylating agent, a hormone, methotrexate, doxorubicin, daunorubicin, cytosine arabinoside, etoposide, 5-4 fluorouracil, melphalan, chlorambucil, cyclophosphamide, cis-platinum, vindesine, mitomycin, bleomycin, purothionin, macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin, and combinations thereof.

61. The method of claim 59, wherein the radiotherapeutic agent is selected from the $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$Bi, $^{32}$P, $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, and $^{197}$Hg.

62. The method of claim 59, wherein the therapeutic agent is a chemotherapeutic agent and the chemotherapeutic agent is administered in an amount ranging from about 10 to about 1000 mg.

63. The method of claim 62, wherein the chemotherapeutic agent is administered in an amount ranging from about 50 to about 500 mg.

64. The method of claim 63, wherein the chemotherapeutic agent is administered in an amount ranging from about 100 to about 250 mg.

65. The method of claim 59, wherein the toxin is selected from the group consisting of Russell's Viper Venom, activated Factor IX, activated Factor X, thrombin, phospholipase C, cobra venom factor, ricin, ricin A chain, Pseudomonas exotoxin, diphtheria toxin, bovine pancreatic ribonuclease, pokeweed antiviral protein, abrin, abrin A chain, gelonin, saporin, modeccin, viscumin, volkensin and combinations thereof.

66. The method of claim 59, wherein the therapeutic agent is a toxin and the toxin is administered in an amount ranging from about 1 to about 500 µg.

67. The method of claim 66, wherein the toxin is administered in an amount ranging from about 10 to about 100 µg.

68. The method of claim 67, wherein the toxin is administered in an amount ranging from about 20 to 50 µg.

69. The method of claim 59, wherein the therapeutic agent is a radiosensitizing agent, and the method further comprises the step of exposing the neoplasm to an additional dose of ionizing radiation.

70. The method of claim 69, wherein the radiosensitizing agent is selected from the group consisting of an anti-angiogenic agent; a DNA protein kinase inhibitor; a tyrosine kinase inhibitor; a DNA repair enzyme inhibitor; nitroimidazole; metronidazole; misonidazole; a genetic construct comprising an enhancer-promoter region which is responsive to radiation, and at least one structural gene whose expression is controlled by the enhancer-promoter; boron-neutron capture reagents; and combinations thereof.

71. The method of claim 70, wherein the genetic construct further comprises a viral vector.

72. The method of claim 69, wherein the neoplasm is exposed to the additional dose of ionizing radiation at a time point falling in a range of about 3 to about 12 hours after initial irradiation of the neoplasm.

73. The method of claim 72, wherein the neoplasm is exposed to the additional dose of ionizing radiation at a time point of about 6 hours after initial irradiation of the neoplasm.

74. The method of claim 59, wherein the therapeutic agent is a radiotherapeutic agent and the radiotherapeutic agent is administered in an amount ranging from about 0.5 to about 100 mg.

75. The method of claim 74, wherein the radiotherapeutic agent is administered in an amount ranging from about 1 to about 50 mg.

76. The method of claim 75, wherein the radiotherapeutic agent is administered in an amount ranging from about 5 to about 10 mg.

77. The method of claim 49, wherein the vertebrate subject is a mammal.

78. The method of claim 77, wherein the mammal is a human.

79. A method of inhibiting angiogenesis in a vertebrate subject, the method comprising the steps of:
   (a) exposing a target tissue in the vertebrate subject to ionizing radiation to target the tissue for a platelet, the target tissue undergoing angiogenesis; and
   (b) administering a platelet to the vertebrate subject before, after, during, or combinations thereof, exposing the target tissue to the ionizing radiation, the platelet comprising an angiogenesis inhibiting amount of an angiogenesis-inhibiting therapeutic agent, whereby the platelet localizes in the target tissue to thereby inhibit angiogenesis by delivering the therapeutic agent to the target tissue.

80. The method of claim 79, wherein the method further comprises the initial step of loading the platelet with an active agent via electroporation.

81. The method of claim 79, wherein the platelet comprising the angiogenesis-inhibiting therapeutic agent is administered after exposing the tissue to ionizing radiation.

82. The method of claim 79, wherein the target tissue comprises a neoplasm.

83. The method of claim 82, wherein the neoplasm is selected from the group consisting of benign intracranial melanomas, arteriovenous malformation, angioma, macular degeneration, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, solid tumors, solid tumor metastases, angiofibromas, retrolental fibroplasia, hemangiomas, Karposi's sarcoma and combinations thereof.

84. The method of claim 79, wherein the vertebrate subject is a mammal.

85. The method of claim 84, wherein the mammal is a human.

86. A method of imaging a target tissue in a vertebrate subject, the method comprising the steps of:
   (a) exposing the target tissue to ionizing radiation to target the tissue for a platelet;
   (b) administering a platelet to the vertebrate subject before, after, during, or combinations thereof, exposing the target tissue to the ionizing radiation, the platelet comprising an imaging agent, whereby the platelet localizes in the target tissue to thereby deliver the imaging agent to the target tissue; and
   (c) detecting the imaging agent in the target tissue.

87. The method of claim 86, wherein the platelet comprising the imaging agent is administered about one hour prior to exposing the target tissue to ionizing radiation.

88. The method of claim 86, wherein the platelet comprising the imaging agent is administered about ten minutes after exposing the target tissue to ionizing radiation.

89. The method of claim 86, wherein the platelet comprising the imaging agent is administered both at about one hour prior to and at about ten minutes after exposing the target tissue to ionizing radiation.

90. The method of claim 86, wherein the method further comprises the initial step of loading the platelet with an active agent via electroporation.

91. The method of claim 86, wherein the platelet comprising the imaging agent is administered after exposing the tissue to ionizing radiation.

92. The method of claim 86, wherein the target tissue is exposed to an ionizing radiation dose ranging from about 1 to about 150 Gy.

93. The method of claim 92, wherein the target tissue is exposed to an ionizing radiation dose ranging from about 2 to about 100 Gy.

94. The method of claim 93, wherein the target tissue is exposed to an ionizing radiation dose ranging from about 4 to about 50 Gy.

95. The method of claim 94, wherein the target tissue is exposed to an ionizing radiation dose ranging from about 10 to about 20 Gy.

96. The method of claim 86, wherein the imaging agent is selected from the group consisting of paramagnetic, radioactive and fluorogenic ions.

97. The method of claim 96, wherein the radioactive imaging agent is selected from the group consisting of gamma-emitters, positron-emitters and x-ray-emitters.

98. The method of claim 97, wherein the radioactive imaging agent is selected from the group consisting of $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb and $^{206}$Bi.

99. The method of claim 96, wherein the radioactive imaging agent is present in the platelet in an amount ranging from about 0.1 to about 100 millicuries.

100. The method of claim 99, wherein the radioactive imaging agent is present in the platelet in an amount ranging from about 1 to about 10 millicuries.

101. The method of claim 100, wherein the radioactive imaging agent is present in the platelet in an amount ranging from about 2 to about 5 millicuries.

102. The method of claim 101, wherein the radioactive imaging agent is present in the platelet in an amount ranging from about 1 to about 5 millicuries.

103. The method of claim 86, wherein the vertebrate subject is a mammal.

104. The method of claim 103, wherein the mammal is a human.

* * * * *